(12) United States Patent
Van Hoy et al.

(10) Patent No.: US 6,415,166 B1
(45) Date of Patent: Jul. 2, 2002

(54) PHOTOPLETHYSMOGRAPHIC DEVICE WITH REMOTE FACSIMILE

(75) Inventors: Gilbert W. Van Hoy, Broomfield; Charles A. Gonzales, Westminster; David L. Newcomb, Louisville; Michael K. Brashears, Denver; Tricia A. Dessel, Boulder, all of CO (US)

(73) Assignee: Datex-Ohmeda, Inc., Louisville, CO (US)

( * ) Notice: Subject to any disclaimer, the term of this patent is extended or adjusted under 35 U.S.C. 154(b) by 0 days.

(21) Appl. No.: 09/386,691

(22) Filed: Aug. 30, 1999

(Under 37 CFR 1.47)

Related U.S. Application Data

(63) Continuation-in-part of application No. 08/938,224, filed on Sep. 26, 1997, now abandoned.

(51) Int. Cl.[7] ................................................. A61B 5/00
(52) U.S. Cl. ........................ 600/323; 600/333; 128/904
(58) Field of Search ................................ 600/300, 301, 600/310, 322, 323, 324, 333; 128/903, 904

(56) References Cited

U.S. PATENT DOCUMENTS

| | | |
|---|---|---|
| 5,078,136 A | 1/1992 | Stone et al. |
| 5,348,004 A | 9/1994 | Hollub |
| 5,515,176 A * | 5/1996 | Galen et al. .................. 128/904 |
| 5,544,649 A * | 8/1996 | David et al. .................. 128/904 |
| 5,581,369 A * | 12/1996 | Righter et al. ............... 128/904 |
| 5,701,894 A | 12/1997 | Cherry et al. |

* cited by examiner

Primary Examiner—Eric F. Winakur
(74) Attorney, Agent, or Firm—Marsh Fischmann & Breyfogle LLP

(57) ABSTRACT

A photoplethysmographic monitoring system such as a pulse oximeter collects data regarding the blood analyte concentration and pulse rate of a patient through the analysis of light transmitted form an emitter through tissue to a photo detector. It is often necessary to review the collected data, such as oxygen saturation, pulse rate and pulsatility value at a location remote to the patient being monitored. The photoplethysmographic system formats the selected data for transmittal to a remote facsimile machine via standard telephone communication systems using an internal or external modem. The formatter is able to function within the processing and memory constraints of pulse oximeters by formatting and transmitting the data in sections. Formatted data may be sent via hard-wired telephone, cellular phone, PCS digital telephones or through satellite communication systems enabling transmittal of data from a portable photoplethysmographic system.

19 Claims, 20 Drawing Sheets

PULSE OXIMETRY INSTAREPORT

601 — H GONZALES
110
DR CASEY
GENERAL

602 — BY _____
COMMENTS _____

STUDY DURATION AND VALUES

| | | | | PR | TIME |
|---|---|---|---|---|---|
| 603 — STUDY START DATE/TIME: | 01/02/99 00:00:00 | LOW SpO₂ | 81% | 134 BPM | 00:58:05 |
| 604 — STUDY END DATE/TIME: | 01/03/99 12:00:00 | AVERAGE SpO₂ | 91% | | |
| | | SpO₂ STD. DEV. | 8% | | |
| 605 — STUDY DURATION: | 12:00:00  606 | | | SpO₂ | TIME |
| | | HIGH PR | 100 BPM | 90% | 02:00:00 |
| | | LOW PR | 61 BPM | 80% | 04:58:06 |
| 607 — # SpO2 VALUES BELOW 85% | 130 | AVERAGE PR | 72 BPM | | |
| 608 — TOTAL DURATION BELOW 85% | 00:13:34 | | | | |

609 — TOTAL TIME bar chart:
- 0-70%: 0%
- 71-75%: 0%
- 76-80%: 0%
- 81-85%: 7%
- 86-90%: 12%
- 91-95%: 20%
- 96-100%: 61%

SpO₂

PULSE OXIMETRY INSTAREPORT                    PAGE 1 OF 2

FIG.6A

701 — H GONZALES
110
DR CASEY
GENERAL

702 — BY: _____
COMMENTS: _____
_____
_____

703 — STUDY DATE:
05/16/98

704 — ALARM LEGEND
HIGH SpO₂.................... ↑ — 716
LOW SpO₂..................... ↓ — 717
NO SENSOR.................... ! — 718
SENSOR OFF.................. ? — 719

705 — 6-SECOND FORMAT
SpO₂

706 — TIME  ▽  50 60 70 80 90 100  SpO₂

707 —
12:34  80                         95
12:34  82                         95
12:34  84                         80↓
12:35  86                         80↓
12:35  88                         95
12:35  90                         95

STUDY DURATION AND VALUES
START DATE/TIME:
708 — 05/16/98  12:34

709 — END DATE/TIME:
05/16/98  12:35

710 — STUDY DURATION:
00:01:00
                                TIME
711 —
LOW SpO₂       80%    84 ▽   12:35
HIGH PR               90 ▽
LOW PR                80 ▽
AVERAGE SpO₂          90%
SpO₂ STD.DEV          —

SUMMARY STATISTICS
%TIME PER SpO₂ RANGE
       0  20  40  60  80  100  %
712 —
90-100  ████████████           67
85-89                           0
80-84   ██████                 33
70-79                           0
0-69                            0

TIME PER SpO₂ RANGE
713 —
90-100%        00:00:24
85-89%         00:00:00
80-84%         00:00:12
70-79%         00:00:00
0-69%          00:00:00

714 — # SpO2 VALUES BELOW 85%:
2

715 — TOTAL DURATION BELOW 85%:
00:00:12

FIG.7

801 — TREND DATA OUTPUT
6 SECONDS PER DATA POINT

802 — P HERNANDEZ
93256
JP CLAIR
GENERAL

803 — 09/03/98

804 —
| Time | SpO2 | PR | PI | | Status |
|---|---|---|---|---|---|
| 14:01:31 | SpO2= 80 | PR= 70 | PI=1.38 | •• | LOW SpO2 |
| 14:01:25 | SpO2= 81 | PR= 70 | PI=1.43 | •• | LOW SpO2 |
| 14:01:19 | SpO2= 81 | PR= 70 | PI=1.48 | •• | LOW SpO2 |
| 14:01:13 | SpO2= 97 | PR= 70 | PI=1.56 | | |
| 14:01:07 | SpO2= 99 | PR= 70 | PI=2.14 | | |
| 14:01:01 | SpO2=100 | PR= 70 | PI=0.47 | | |
| 14:00:55 | SpO2=100 | PR= 69 | PI=....... | | |
| 14:00:49 | SpO2=..... | PR=.... | PI=....... | •• | NO SENSOR |
| 14:00:43 | SpO2=..... | PR=.... | PI=....... | •• | NO SENSOR |
| 14:00:37 | SpO2=..... | PR=.... | PI=....... | •• | NO SENSOR |

END TREND DATA

FIG.8

PHOTOPLETHYSMOGRAPHIC DEVICE WITH REMOTE FACSIMILE

CROSS REFERENCE TO RELATED APPLICATION

This application is a continuation-in-part of application Ser. No. 08/938,224, filed on Sep. 26, 1997, and titled "PHOTOPLETHYSMOGRAPHIC DEVICE WITH REMOTE FACSIMILE", now abandoned, which is incorporated herein by reference in its entirety.

FIELD OF THE INVENTION

This invention relates to the collection and transmission of data in medical monitoring equipment and, in particular, to the collection, selection, arrangement, formatting, and transmission of data in photoplethysmographic systems which relate to the concentrations of certain blood analyte levels of a patient.

BACKGROUND OF THE INVENTION

It is a problem in the field of monitoring systems to transmit photoplethysmographic monitoring data to a physician, hospital, or other care giver from a remote location using only the hardware associated with the standard photoplethysmographic devices. To date no photoplethysmographic monitors exist which are capable of pre-formatting the data collected and blood analyte measurements generated by a photoplethysmographic monitor.

A facsimile is a digital representation of an image. Data and text in a facsimile is not stored as words and letters in ASCII format, but rather the image of the text, data, graphs, etc. is stored as a gray-scale bit map. It is possible to purchase a standard modem for the transmittal of data to a remote location. However, there is no way to send the information directly to a facsimile machine due to the special facsimile data format which is required.

The problems associated with the limitations of standard photoplethysmographic systems has led to a number of prior art alternatives which have their own limitations and drawbacks.

The Medical Data Archiving Corporation (MDAC) Oximetry Recording & Reporting System (OxiScan™) provides a method and system for transmission of oximetry data via standard telephone lines. The OxiScan™ system requires the connection of the photoplethysmographic monitor to a processing terminal. Additionally, the output of the processing terminal is not sent to the ultimate care provider, but rather, is directed to the MDAC Reporting Service which then sends an oximetry report to a facsimile machine within fifteen minutes. The delay caused by the intermediate processing at a second remote location and the possibility of error introduced by the additional transmission step reduces the usefulness of such a system.

In most commercial pulse oximeters such as the Ohmeda® 3800 or the Nellcor –3000 there is an RS232 serial port which may be used to download collected photoplethysmographic data from a pulse oximeter to another computing device. However, there is presently no photoplethysmographic system that enables a user, such as a remote acute care provider, to convey photoplethysmographic data directly from the remote field location to the ultimate care provider in the hospital or physician's office.

SUMMARY OF THE INVENTION

The above described problems are solved and a technical advance achieved in the field by the photoplethysmographic system of the present invention which conveys photoplethysmographic data to the standard facsimile machine of a remote user in a simple, direct, and immediate manner. This photoplethysmographic system produces a facsimile data format serial output which can be transmitted to the remote facsimile via telephone lines via an external modem or via a modem internal to the photoplethysmographic monitor. Photoplethysmographic data may also be transmitted to a remote host system via the internal or external modem. The remote host system may also retrieve the data through contacting the system of the present invention directly. Lastly, through an internal printer, photoplethysmographic data may be printed out in hard copy form.

In a preferred embodiment of the invention, a photoplethysmographic monitoring system provides the facsimile data format for oximetry data to an external modem via its serial port. In another embodiment of the invention, the photoplethysmographic monitor contains the modem internally and, therefore, can transmit formatted reports directly to the facsimile machine of a remote user without additional hardware.

DESCRIPTION OF THE DRAWINGS

FIGS. 6A and 6B depict the facsimile report format of a device according to an embodiment of the present invention.

FIG. 7 depicts the internal printer report format of a device according to an embodiment of the present invention.

FIG. 8 depicts the remote host system report format of a device according to an embodiment of the present invention.

DETAILED DESCRIPTION

Figure 1:
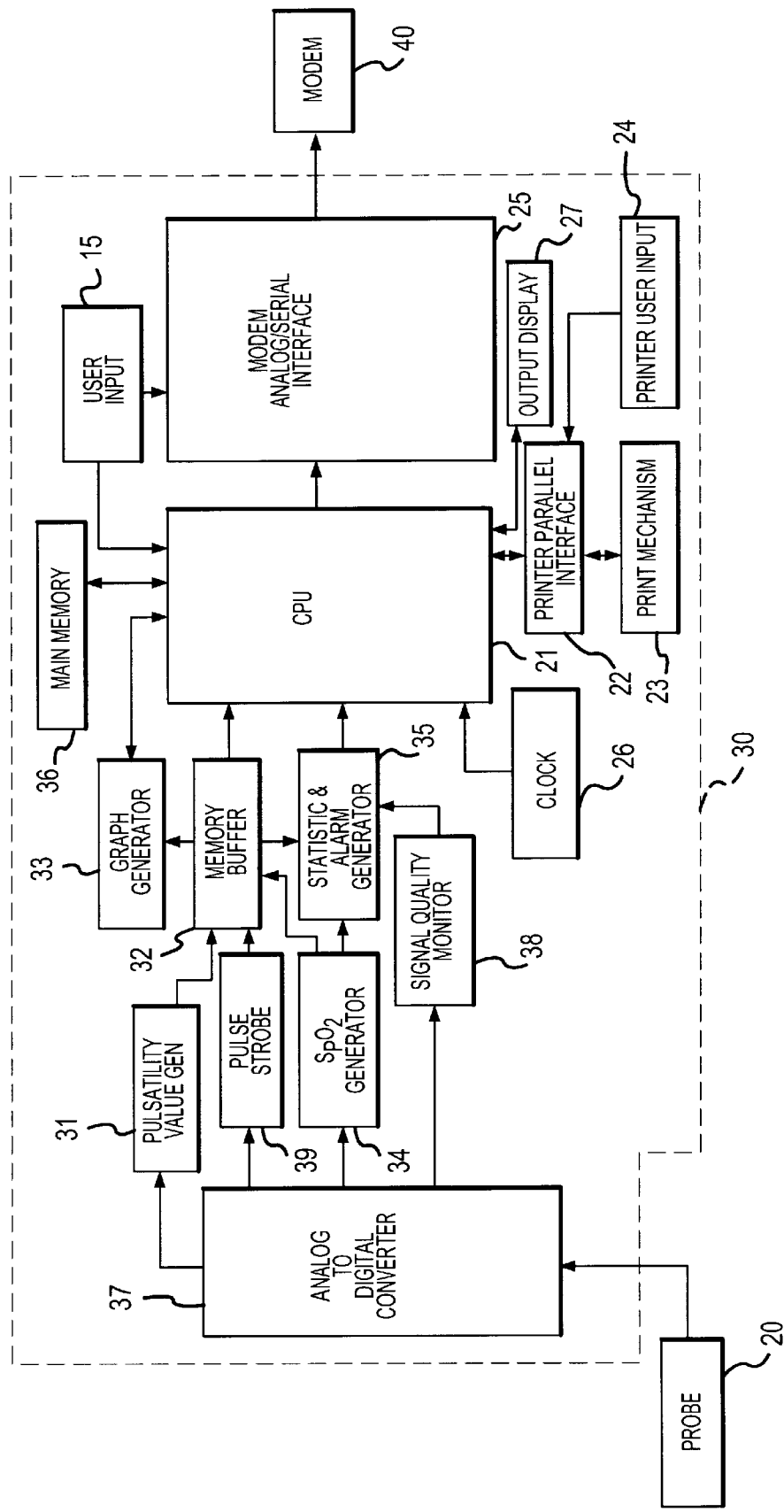
FIG. 1 is a functional block diagram of one embodiment of the present invention in which the formatted data is directed to an external modem or to an internal printer.

The data collected by a pulse oximeter, which is a type of photoplethysmographic monitoring system, is used to generate a saturation value for oxygenated hemoglobin ($SpO_2$) which is directly related to the oxygen content of the patient's blood, a pulse rate, and a pulsatility value. Other types of photoplethysmographic monitors may include blood analyte concentrations for carboxyhemoglobin, methemoglobin, or other blood analytes. In most pulse oximeters a number representing the oxygen content of the blood of a patient ($SpO_2$) is displayed. A photoplethysmographic waveform of the pulsatile variations in the collected data over time or trend data over a period of time may also be displayed. The pulse of the patient may also be displayed, and in certain Ohmeda® pulse oximeters, a Perfusion Index PI™ pulsatility value is displayed. The PI™ pulsatility value indicates a quantified level of perfusion of the tissue of a patient through the inflow of blood into the tissue. All of this information is useful to the medical practitioner in determining the condition and proper treatment of a patient.

The present invention enables the user of a photoplethysmographic system to send collected photoplethysmographic data from the system to a remotely located facsimile machine thereby providing a formatted hard copy printout of the photoplethysmographic data without the use of auxiliary computing devices, such as a personal computer or central monitoring station. Thereby, useful photoplethysmographic data, such as $SpO_2$ levels, pulse rates, and pulsatility values

- can be transmitted in a useful format from any location to a remotely located medical practitioner using standard telecommunications equipment. Data may also be sent directly to a remote host system, such as a personal computer, through
- the modem, or directly downloaded to a personal computer through an RS232 interface. In addition, the present invention will automatically answer an incoming call from a personal computer, and allow the personal computer to access the photoplethysmographic data. An optional internal printer can provide on-demand hard copy output of the collected data.

The monitoring apparatus described herein as the preferred embodiment is a pulse oximeter instrument which measures the oxygen saturation of the arterial blood of a patient. The pulse oximeter instrument operates by illuminating the arteriolar bed of a perfused appendage, ear lobe, or nasal septum of the patient with light from light sources characterized by spectra having distinct center wavelengths. The center wavelengths are selected so that the light emitted by one light source is highly absorbed by oxygenated hemoglobin contained in the arterial blood, while the other is selected with respect to its absorbency by deoxygenated hemoglobin. The pulse oximeter instrument then measures the magnitude of the light that passes through the illuminated tissue. The pulsatile component of the light output from the tissue is used to determine the oxygen saturation of the arterial blood flow.

Figure 2:
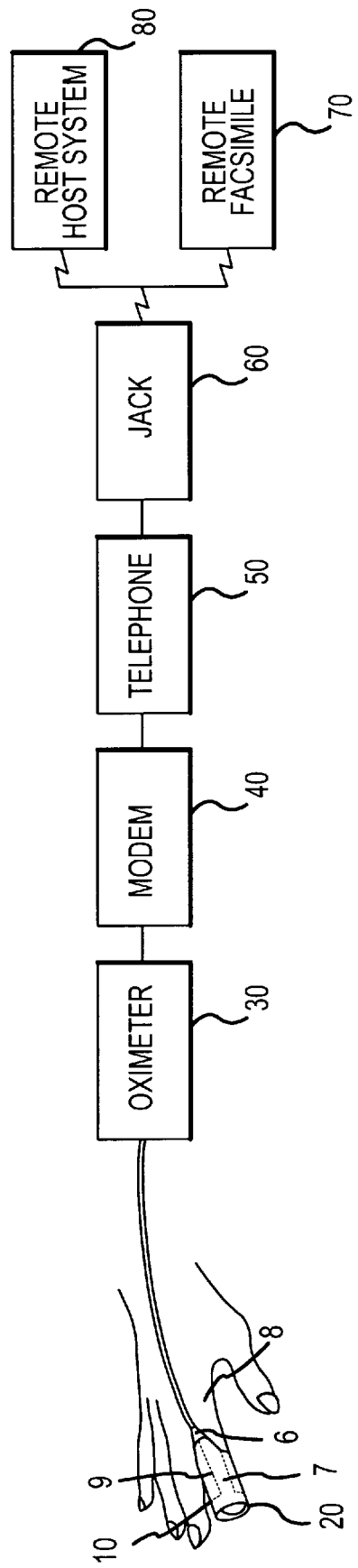
FIG. 2 is a block diagram of the embodiment of FIG. 1 further depicting functional components of the system of FIG. 1.

Referring to FIGS. 1 and 2, a probe 20 containing a plurality of light sources 9 and 10, such as LED or laser diodes, and a photo detector 7 is attached to an appendage of the patient, such as a finger 8. The appendage is rich in arterial blood flow so that the light transmissivity of the arterial blood, and thereby the oxygen saturation thereof, can be directly measured. The light sources 9 and 10 and photo detector 7 may, alternatively, be placed on the ear lobe or nasal septum of the patient. The output signal produced by the photo detector 7 is transmitted via cable 6 and is processed by the pulse oximeter instrument 30, producing a numeric value indicative of the oxygen saturation of the arterial blood. It is a collection of these oxygen saturation levels ($SpO_2$ levels) over time that is transmitted to a remote location or retrieved from a remote location or printed out on an internal printer.

The functional block diagram of the pulse oximeter instrument 30 of FIG. 1 provides a description of the internal processing necessary to provide a complete facsimile data format output to modem 40 and to remote facsimile 70, to provide an ASCII data format output to modem 40 and to remote host system 80, and to provide an ASCII data format output to print mechanism 23.

Raw input data from probe 20 is converted to a digital representation by analog-to-digital converter 37. The digital data set representing the output from photo detector 7 of probe 20 is then used by the software internal to the pulse oximeter instrument 30 to calculate the $SpO_2$ level of the patient's blood in a well known way. For instance, the techniques discussed in U.S. Pat. No. 5,503,148 issued to Pologe et. al., hereby incorporated by reference, may be used for calculating $SpO_2$ levels.

The digital data set from the analog-to-digital converter 37 is used by the $SpO_2$ generator 34 to generate $SpO_2$ saturation levels at specific time intervals of at least every six seconds. The $SpO_2$ saturation levels generated by the $SpO_2$ generator 34 are then forwarded to a memory buffer 32 where a time-tagged series of $SpO_2$ blood saturation values is stored for later output to central processing unit 21 and on to main memory 36, modem analog/serial interface 25, output display 27, and printer parallel interface 22, and for use by graph generator 33 and statistic and alarm generator 35. Output display 27 is typically a combination of an LED display and an LCD display, but could be one or the other only. Photoplethysmographic waveform and trend data are easily displayed on the LCD type display. Saturation and pulse rate values and alarm indicators are readily displayed on the LED type display.

The $SpO_2$ saturation levels generated by the $SpO_2$ generator 34 are forwarded from memory buffer 32 to a statistic and alarm generator 35 where a set of statistical characteristics for a data set are defined for the buffered set of data. For example, a histogram may be generated as well as a breakdown by range of the amount of time the $SpO_2$ level was within certain ranges. Other statistical characteristics such as the highest and lowest $SpO_2$ levels and durations for each of the high and low levels for a given set of data can also be generated by the statistic and alarm generator 35. Examples of alarms which can be generated by the statistic and alarm generator 35 include "Low $SpO_2$", "High $SpO_2$", "No Sensor" and "Sensor Off" warnings. These latter two warnings are generated by the data emerging from the signal quality monitor 38.

Signal quality monitor 38 receives data from the analog-to-digital converter which is indicative of the quality of the input data signal. The quality of the signal can be a measure of the signal to noise ratio, intensity and/or frequency of motion artifacts, or other measure of the credibility of the input data, regardless of the signal strength. The signal quality monitor 38, in response to the received data, produces one of a plurality of drive signals to generate an indication of the quality of the input data signal in order to determine if an alarm such as "No Sensor" or "Sensor Off" should be displayed to the user.

There are other characteristics of the input signal received from probe 20 that are of interest to the user of the pulse oximeter 30, such as the patients' pulse rate and pulsatility value. Data from analog-to-digital converter 37 is also supplied to pulse strobe 39 to provide a time-tagged pulse value for the patient which is then stored in memory buffer 32 for later transfer through central processing unit 21 to specific memory locations in main memory 36. The data will later be used by modem analog/serial interface 25 and printer parallel interface 22. The statistic and alarm generator 35 also uses the set of pulse values to develop a high and low pulse statistic and rate duration as well as high and low pulse alarms. Data from analog-to-digital converter 37 is also forwarded to a pulsatility value generator 31 where the pulsatility value is generated according to one or more known methods, including, but not limited to, percent modulation.

Graph generator 33 provides a bar graph or other graphical representation of photoplethysmographic data which can then be stored in main memory 36 and formatted for transmission to the remote facsimile via modem 40. Internal clock 26 is used to time-tag data and provide the date of data collection, the time the data collection began, and the duration of the data collection.

User input 15 provides a mechanism for the user, generally, the nurse, home-care aide or physician, to input data regarding the patient and the time and date of the photoplethysmographic study. Additionally, user input 15 permits the user to select the duration of the study, to select the format of data to be displayed on output display 27, to select modem characteristics, and set up pulse oximeter 30 for transmission of data via modem 40 or in response to receiving a call from remote host system 80. User input 15 may comprise one or more of the following input devices: touch-sensitive screen, keyboard, touch-pad, mouse, trackball, joystick, or axially actuatable rotary dial (for example, as disclosed in U.S. Pat. No. 5,627,531 to Reichert et al., and hereby incorporated by reference). In an alternate embodiment the user input 15 is external to pulse oximeter 30 and communicates through the standard RS232 port found on most pulse oximeters. In this alternate embodiment user input 15 may be a personal computer or some other communication device having a user interface and a serial communication port.

Print mechanism 23 can provide on-demand hard copy output of the data collected by probe 20 and processed by pulse oximeter 30. Printer mechanism 23 is typically a thermal single column dot matrix printer. Printer user input 24 is only active when waveform data or trend data is being displayed on output display 27.

The user may select one of several options with printer user input 24. The user may select to print out real time data while monitoring the patient. The real time data may be printed out in $SpO_2$ format or PI™ format in either six second or thirty second intervals. Selecting a summation option during real time printing immediately stops the real time printing. Summary statistics are then printed out encompassing all the data that was printed out in real time up to the time when the summation option was selected. The user may also choose to print trend data over a selected period of time. The user can further select to print all the trend data over the selected period of time or only summary statistics for the selected period of time.

FIG. 2 depicts a system according to the present invention wherein probe 20 is connected to pulse oximeter 30. Upon selection of a send fax option, pulse oximeter 30 generates data in a facsimile data format which is sent via modem 40 and telephone 50 through a standard telephone jack 60 through the telecommunication switching network of local and/or long distance carriers to remote facsimile 70. Upon selection of a send to host system option, pulse oximeter 30 generates data in an ASCII data format which is sent via modem 40 and telephone 50 through a standard telephone jack 60 through the telecommunication switching network of local and/or long distance carriers to remote host system 80. Upon selection of a wait for call option, pulse oximeter 30, when called by remote host system 80, generates data in an ASCII data format which is sent via modem 40 and telephone 50 through a standard telephone jack 60 through the telecommunication switching network of local and/or long distance carriers to remote host system 80.

Figure 3:
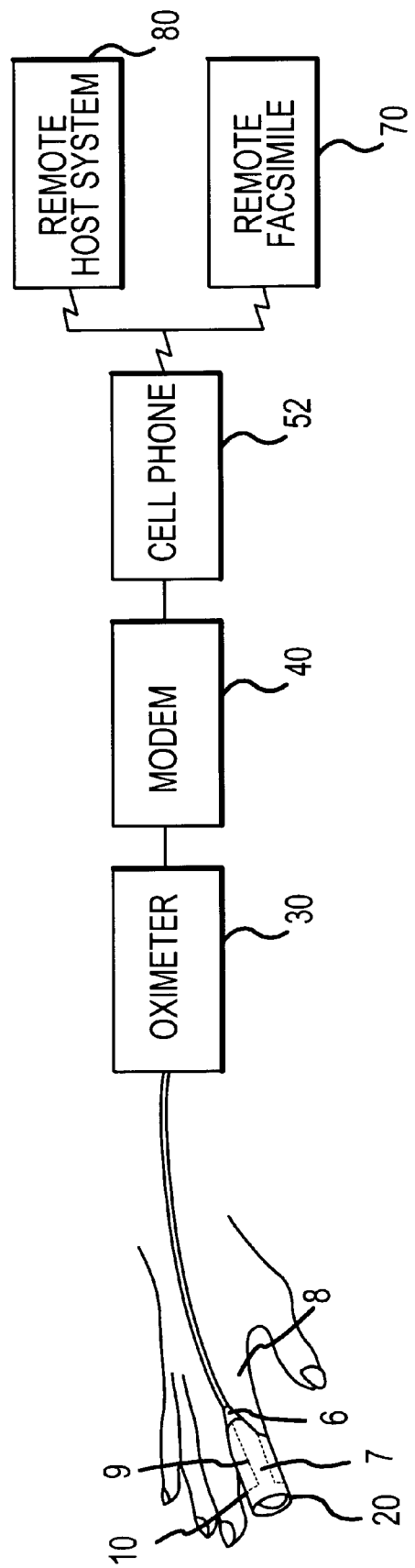
FIG. 3 is a block diagram of the embodiment of FIG. 1 further depicting alternative functional components of the system of FIG. 1.

FIG. 3 depicts an additional connection scheme where external modem 40 is compatible with cellular communication devices for transmission of the data in facsimile data format to remote facsimile 70 or ASCII data format to remote host system 80. It is also possible to use other telecommunications devices, such as digital PCS telephones, or satellite telephony services such as Globalstar® or Iridium®. Such systems allow the pulse oximeter to be used as a portable unit with the ability to provide facsimile data format output or ASCII data format output to any remote facsimile machine independent of hard-wired connections to existing telephone systems.

Figure 4:
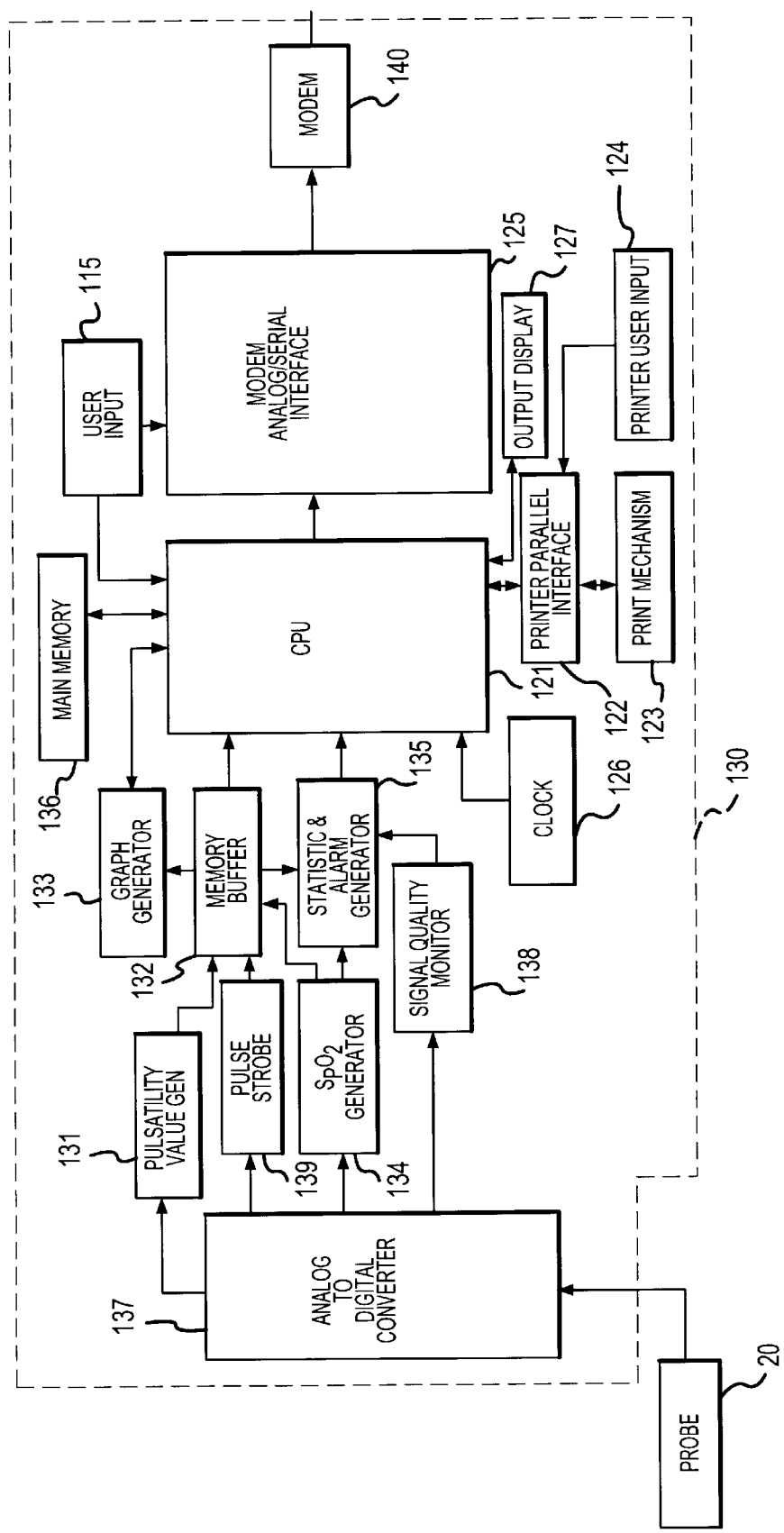
FIG. 4 is a functional block diagram of an alternative embodiment of the present invention in which the modem is internal to the photoplethysmographic device.

FIG. 4 depicts an alternate embodiment of a pulse oximeter according to the present invention. Probe 20 is connected to pulse oximeter 130 which contains essentially identical circuitry and software to the above discussed embodiment of FIG. 1 including user input 115, central processing unit 121, printer interface 122, print mechanism 123, printer user input 124, modem analog/serial interface 125, internal clock 126, output display 127, pulsatility value generator 131, memory buffer 132, graph generator 133, $SpO_2$ generator 134, statistic and alarm generator 135, main memory 136, analog-to-digital converter 137, signal quality monitor 138, and pulse strobe 139. In this alternate embodiment, however, modem 140 is internal to pulse oximeter 130, thereby reducing the number of external boxes and connections required for use of the remote facsimile function.

Figure 5:
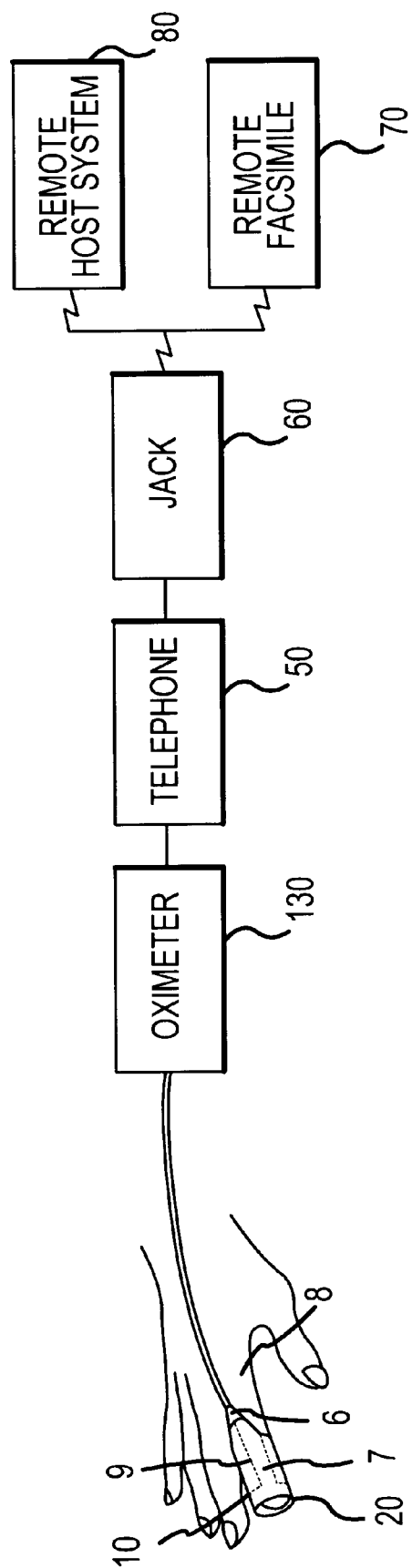
FIG. 5 is a block diagram of the alternative embodiment of FIG. 4 further depicting functional components of the system of FIG. 4.

FIG. 5 is a block diagram of the alternative embodiment of FIG. 4 further depicting functional components of the system of FIG. 4. Referring now to FIG. 5, pulse oximeter 130 with an internal modem is connected to the remote facsimile 70 or the remote host system 80 via telephone 50 and telephone jack 60.

Figure 6B:
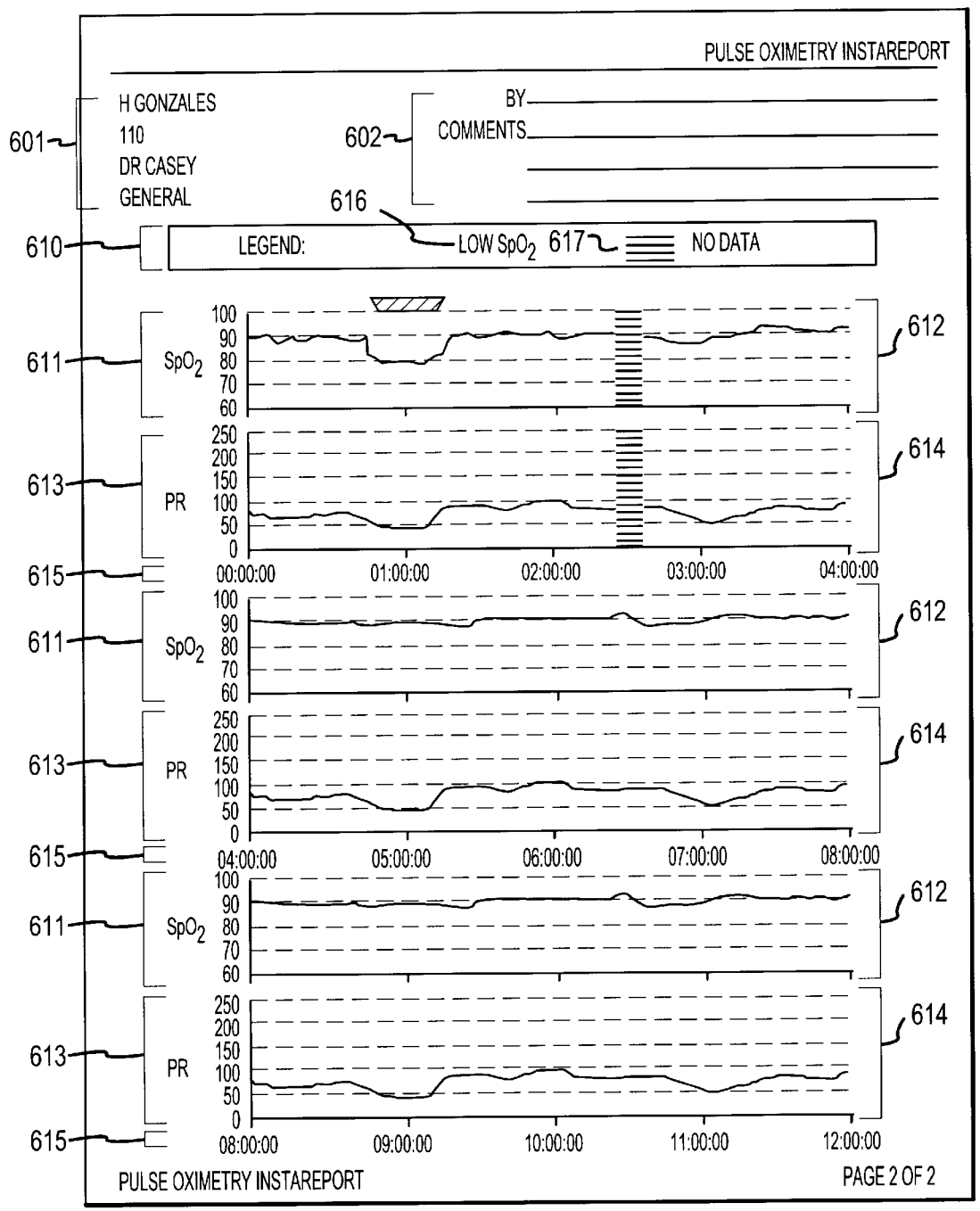

FIGS. 6A and 6B depict one embodiment of a facsimile report format for photoplethysmographic data for a device according to the present invention. Referring now to FIGS. 6A and 6B, Label Information Field 601 provides up to four lines of alphanumeric text, such as patient name, patient number, doctor name, and hospital. By And Comments Field 602 provides up to four lines of alphanumeric text, such as clinician name and any relevant comments. Data for Label Information Field 601 and By And Comments Field 602 is entered either through user input 15 which is internal to pulse oximeter 30, or through a personal computer keyboard which is in serial communication with pulse oximeter 30.

Study Start Time Field 603, Study End Time Field 604, and Study Duration Field 605 provide the date and time the data collection began, the date and time the data collection ended, and the duration of the data collection respectively. These values are derived from the internal clock 26 of pulse oximeter 30, which is also used to time-tag data.

Statistic and alarm generator 35 is responsible for generating the data found in Study Highlights Field 606, which includes the lowest $SpO_2$ value for the data printed with a corresponding Pulse Rate (PR) and time stamp. The average $SpO_2$ value, the $SpO_2$ standard deviation, the high PR rate with corresponding $SpO_2$ value and time stamp, the low PR rate with corresponding $SpO_2$ value and time stamp, and average PR are also reported. The standard deviation represents the scatter of the $SpO_2$ data points. A high standard deviation represents a wide range of $SpO_2$ values.

$SpO_2$ Values Below Field 607 shows the total number of $SpO_2$ values below the low $SpO_2$ alarm limit. Total Duration Below Field 608 shows the total amount of time for all $SpO_2$ values below the low $SpO_2$ alarm limit. The data for these fields is forwarded by the statistic and alarm generator 35 to the modem analog/serial interface 25 which then places the data in the correct fields.

Percent Time Per $SpO_2$ Range Block 609 contains a graph of the percentage of time the patient's $SpO_2$ was recorded in each of the ranges indicated. This graph is generated by graph generator 33 using data from memory buffer 32.

Alarm Legend 610 provides a legend of trend events that may occur. An event's legend symbol appears on the report at the time of occurrence. Low $SpO_2$ Symbol 616 indicates an $SpO_2$ value was recorded that was below the low alarm limit. No Data Symbol 617 indicates that no data was recorded.

$SpO_2$ Scale 611 indicates the percent scale for $SpO_2$ values displayed in the $SpO_2$ Time Graph 612. PR Range 613 indicates the beats per minute range used for PR values displayed in the PR Time Graph 614. Time Scale 615 shows the time scale used for $SpO_2$ Time Graph 612 and PR Time Graph 614. These graphs are also generated by graph generator 33 using data from memory buffer 32.

The modem analog/serial interface 25 of FIG. 1 sends the final data in the facsimile data format to remote facsimile 70 where it appears on paper in the facsimile report format of FIGS. 6A and 6B. The data format and protocol for transmissions to facsimile machines of the present invention are governed by standards established by the International Telegraph and Telephone Consultative Committee (CCITT). Telephone system standards for generating bit-images and the transmission protocol for facsimile machines may be found in publications CCITT T.4 and CCITT T.30 respectively.

Remote facsimile 70 receives a continuous stream of data from modem 40 although the facsimile data format is not generated in its entirety prior to initiation of the send data command discussed below. Rather, the data is accessed, formatted, and transmitted line by line. This enables the pulse oximeter 30 to provide a complete and detailed output to remote facsimile 70 while minimizing the use of the limited internal main memory 36 of pulse oximeter 30 until the facsimile data format is actually needed.

When remote facsimile 70 is called by pulse oximeter 30 through modem 40, one of the pieces of information exchanged in the handshaking is the speed at which remote facsimile 70 will receive data. If the data stream from pulse oximeter 30 stops, remote facsimile 70 will disconnect the telephone line. Therefore, if pulse oximeter 30 produces data line by line at a rate slower than remote facsimile 70 requires, the telephone line will be disconnected. To prevent this from happening, pulse oximeter 30 inserts and transmits zeros as filler data at the end of a first line of formatted data if the next line of formatted data is not yet ready to send. If pulse oximeter 30 generates data line by line faster than remote facsimile 70 can receive it, pulse oximeter 30 introduces delays in releasing the formatted data line by line so that remote facsimile 70 will not be overrun with data faster than it can print it.

FIG. 7 depicts one embodiment of an internal printer report format of photoplethysmographic data for a device according to the present invention. Referring now to FIG. 7, Label Information Field 701 provides up to four lines of alphanumeric text, such as patient name, patient number, doctor name, and hospital. By And Comments Field 702 provides up to four lines of alphanumeric text, such as clinician name and any relevant comments. Data for Label Information Field 701 and By And Comments Field 702 is entered either through user input 15 which is internal to the pulse oximeter 30, or through a personal computer keyboard which is in serial communication with the pulse oximeter 30.

Study Date Field 703 provides the date and time the initial data was collected. Study Start Time Field 708, Study End Time Field 709, and Study Duration Field 710 provide the date and time the data collection began, the date and time the data collection ended, and the duration of the data collection respectively. These date and time values are derived from the internal clock 26 of pulse oximeter 30, which is also used to time-tag data.

Alarm Legend 704 lists trend events that may occur and a symbol for each event. The symbols appear in Graph Field 707 at the time of occurrence. The symbols include High $SpO_2$ Symbol 716(↑), Low $SpO_2$ Symbol 717(↓), No Sensor Symbol 718 (!), and Sensor Off Symbol 719 (?).

Print Format Field 705 indicates the frequency at which data points are printed for this report, such as every six seconds or every thirty seconds. Header Field 706 indicates headings for the time, pulse rate, percentage scale for $SpO_2$ values, and $SpO_2$ value used for Graph Field 707 for this report. Graph Field 707 is generated by graph generator 33 using data from memory buffer 32 and contains graphical and numerical $SpO_2$ values with corresponding PR values and alarm events.

Statistic and alarm generator 35 is responsible for generating the data found in Study Highlights Field 711, which includes the lowest $SpO_2$ value for the data printed with a corresponding Pulse Rate (PR) and time stamp. The high PR rate, the low PR rate, the average $SpO_2$ value, and the $SpO_2$ standard deviation are also reported.

Percent Time Per $SpO_2$ Range Block 712 contains a graph of the percentage of time the patient's $SpO_2$ was recorded in each of the ranges indicated. Time Per $SpO_2$ Range Block 713 contains a graph of the total duration of $SpO_2$ values that occurred within each of the ranges indicated. These two graphs are generated by graph generator 33 using data from memory buffer 32.

$SpO_2$ Values Below Field 714 shows the total number of $SpO_2$ values below the low $SpO_2$ alarm limit. Total Duration Below Field 715 shows the total amount of time for all $SpO_2$ values below the low $SpO_2$ alarm limit. The data for these fields is forwarded by the statistic and alarm generator 35 to the modem analog/serial interface 25 which then places the data in the correct fields.

The printer parallel interface 22 of FIG. 1 sends the final data in the ASCII data format to printer mechanism 23 where it appears on paper in the internal printer report format of FIG. 7.

FIG. 8 depicts one embodiment of a remote computer report format of photoplethysmographic data for a device according to the present invention. Referring now to FIG. 8, Print Format Field 801 indicates the frequency at which data points are printed for this trend data report, such as every six seconds or every thirty seconds. Label Information Field 802 provides up to four lines of alphanumeric text, such as patient name, patient number, doctor name, and hospital. Data for Label Information Field 802 is entered either through the user input 15 internal to pulse oximeter 30, or through a personal computer keyboard which is in serial communication with pulse oximeter 30.

Study Date Field 803 provides the date the initial data was collected. This date value is derived from internal clock 26 of pulse oximeter 30, which is also used to time-tag data. Data Field 804 contains the capture time for numerical $SpO_2$ values, along with corresponding PR values, pulsatility values, and alarm events.

The modem analog/serial interface 25 of FIG. 1 sends the final data in the ASCII data format to remote host system 80 where when it is printed out appears on paper in the remote computer report format of FIG. 8. This report is sent when the user dials up remote host system 80 from pulse oximeter 30 and modem 40, or when a remote host system 80 calls pulse oximeter 30 through modem 40.

FIGS. 9 through 15 depict the various user input menus according to one embodiment of the present invention.

Figure 9:
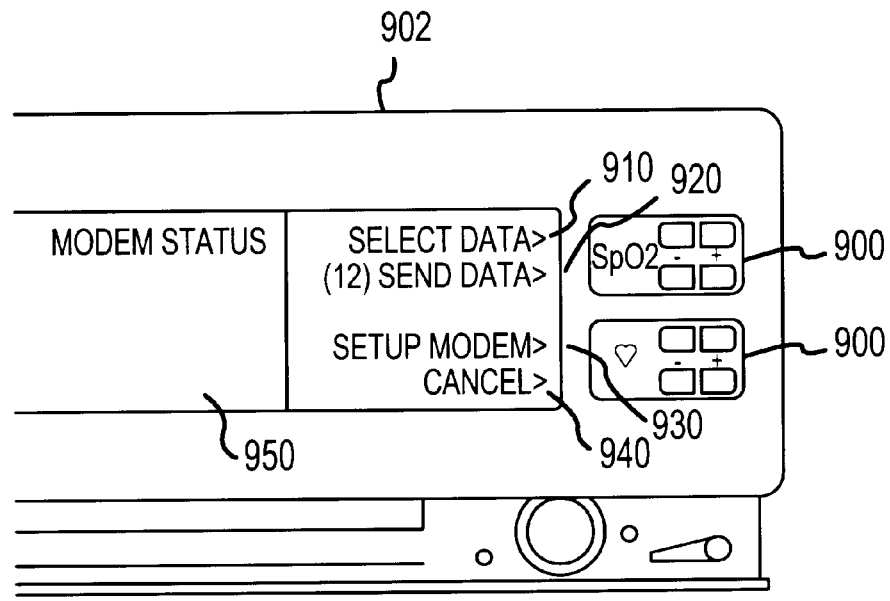
FIGS. 9 through 15 depict various user interface screens provided in an embodiment of the present invention.

Referring now to FIG. 9, the eight function keys 900 on front panel 902 of pulse oximeter 30 are used by the user to select various functions and selections depending on the information depicted on display screen 950. In normal operation these keys are used to set alarm limits. However, in the facsimile mode the keys have different functions. A menu key (not shown in FIG. 9) located on front panel 902 et al. of pulse oximeter 30 is pressed to enter the main menu. In the main menu four selections are displayed: MODEM, LABELS, SETTINGS, and DATE (also not shown in FIG. 9). The facsimile capability is reached by selecting MODEM.

Upon selecting the MODEM selection on the main menu of pulse oximeter 30, display screen 950 displays in FIG. 9 a modem status and four function key selections: SELECT DATA 910, SEND DATA 920, SETUP MODEM 930, and CANCEL 940. When pulse oximeter 30 is searching for modem 40, the message "SEARCHING" is displayed in display screen 950. When modem 40 is found, the message "CONNECTED" is displayed in display screen 950.

Selecting SELECT DATA 910 allows the user to select the amount of the pulse oximetry study that has been stored that the user desires to be formatted for output. The default duration is 12 hours unless there is less than 12 hours of data in memory buffer 32, and then the default is equivalent to the amount of data stored in memory buffer 32. The maximum amount of time allowed for the duration of the study is 24 hours. Selecting SELECT DATA 910 causes display screen 950 to display the content shown in FIG. 10.

Figure 10:
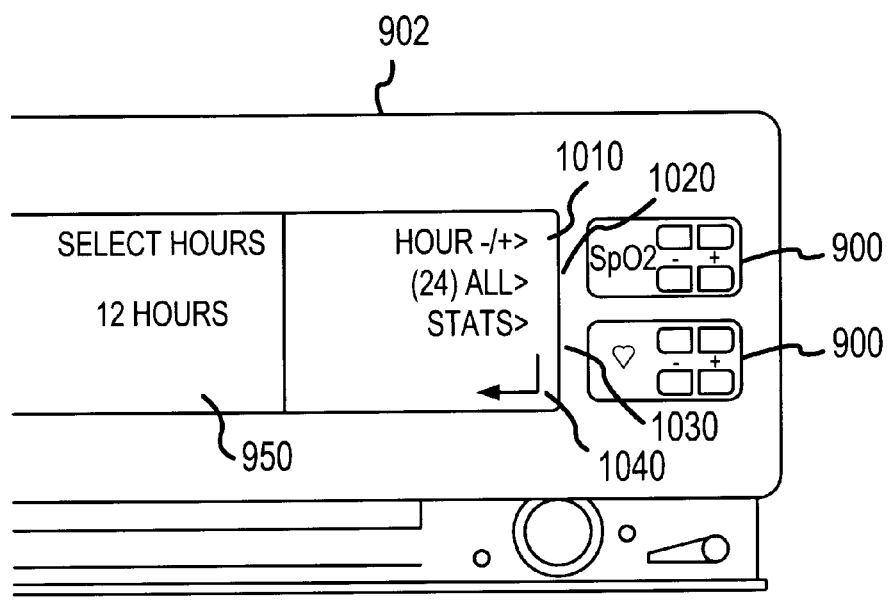

Referring now to FIG. 10, selecting HOUR-/+1010 enables the user to select the amount of time, in one hour increments or decrements, for which data will be formatted for output. The amount of time selected is displayed in display screen 950.

Selecting (n) ALL 1020 causes all data stored in main memory 36 to be selected. The number n in parentheses to the left of "ALL" indicates the amount of data stored in main memory 36 to the nearest hour. For example (5) ALL indicates that there are approximately five hours of data stored in main memory 36.

By selecting STATS 1030 in FIG. 10, only print headings and summary statistics for each data record within the hours selected will be output. Selecting STATS 1030 causes the word "STATS" to appear in display screen 950. Selecting return arrow 1040 returns the user to the contents of display screen 950 shown in FIG. 9.

Figure 11:
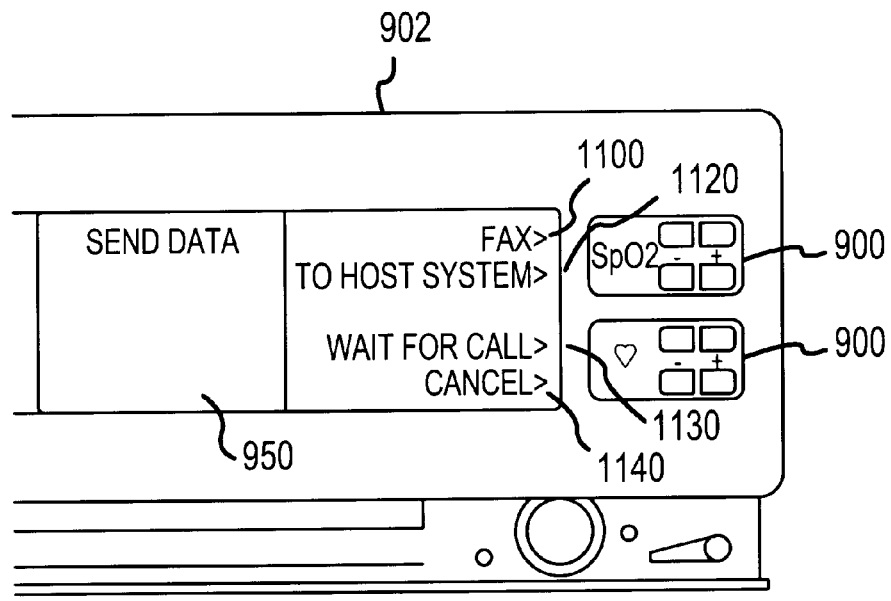

Selecting SEND DATA 920 (FIG. 9) causes display screen 950 to display the content shown in FIG. 11. Referring now to FIG. 11, the user is prompted with options regarding the sending of the selected data. These options are: FAX 1110, TO HOST SYSTEM 1120, WAIT FOR CALL 1130, and CANCEL 1140. Selecting FAX 1110 will cause the data selected to be formatted in facsimile data format for transmission, and causes display screen 950 to display the content shown in FIG. 12.

Figure 12:
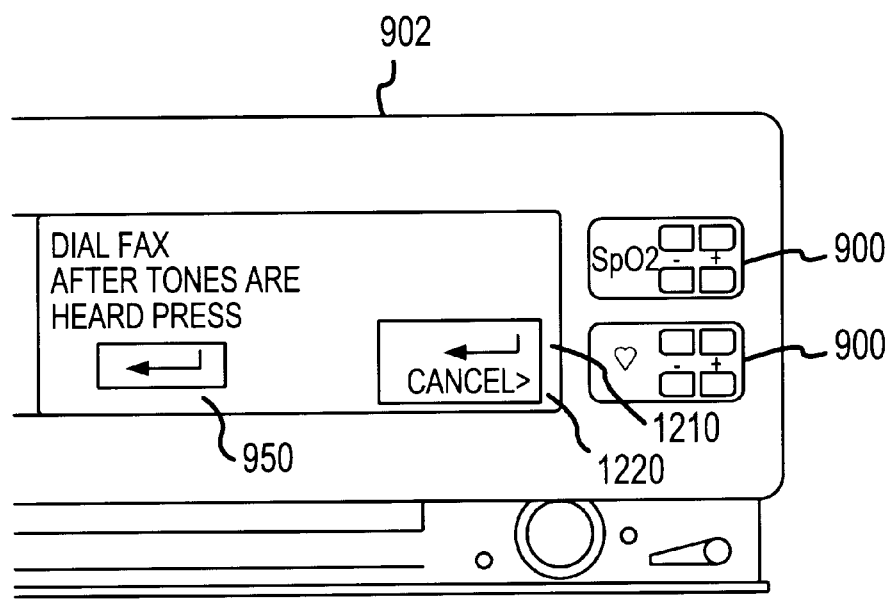

Referring now to FIG. 12, screen display 950 displays a message prompting the user to dial the remote facsimile 70 using telephone 50 and to select return arrow 1210 when the connection tone of the remote facsimile 70 is heard. In another embodiment, display screen 950 displays blanks for the user to enter the phone number for the remote facsimile 70 using user input 15 internal to pulse oximeter 30. After entering the number, selecting return arrow 1210 dials the number entered. Selecting CANCEL 1220 cancels the data sending process and returns the user to the contents of display screen 950 shown in FIG. 9.

Figure 13:
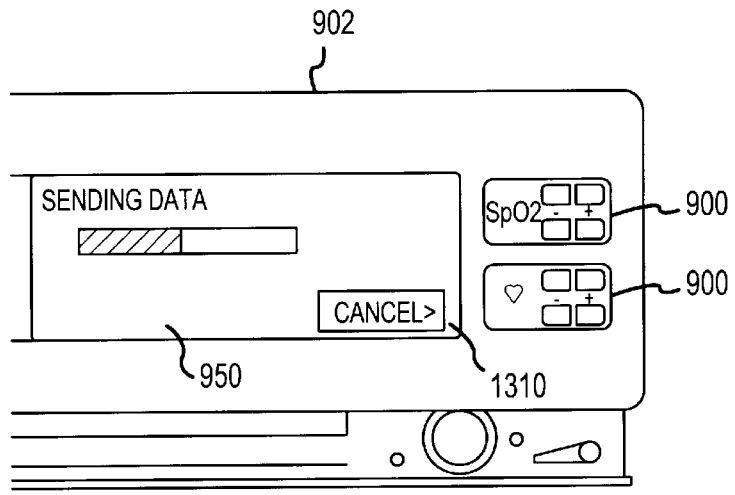

Upon selecting return arrow 1210, modem analog/serial interface 25 will begin sending the formatted data selected line by line to remote facsimile 70, and causes display screen 950 to display the content shown in FIG. 13.

Referring now to FIG. 13, DISPLAY screen 950 shows a "SENDING DATA" message and a scroll bar. The data transmission is complete when the shaded portion of the bar scrolls all the way from the left to the right. Selecting CANCEL 1310 will cause a "FAX CANCELED" message (not shown in FIG. 13) to be displayed to the user in display screen 950, and the data flow to the modem will be stopped. After a brief predetermined period of time, display screen 950 displays the content as shown in FIG. 9.

Selecting TO HOST SYSTEM 1120 (FIG. 11) will enable data to be sent to remote host system 80, which may be a central monitoring station. Selecting TO HOST SYSTEM 1120 causes display screen 950 to display the content shown in FIG. 14.

Figure 14:
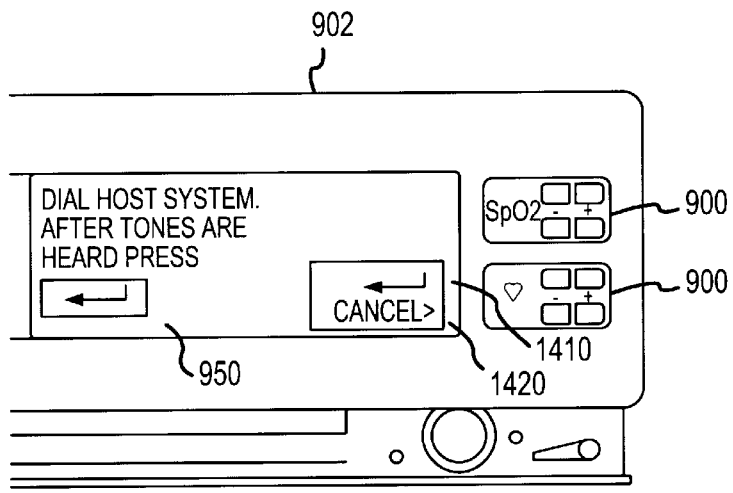

Referring now to FIG. 14, Screen display 950 prompts the user to dial remote host system 80 using telephone 50, and to select return arrow 1410 when the connection tone for remote host system 80 is heard. Data is formatted differently when TO HOST SYSTEM 1120 is selected as opposed to selecting FAX 1110. Selecting CANCEL 1420 cancels the data sending process and returns the user to the contents of display screen 950 shown in FIG. 9.

Selecting WAIT FOR CALL 1130 (FIG. 11) will enable data to be sent by pulse oximeter 30 to remote host system 80 when remote host system 80 contacts pulse oximeter 30. Selecting WAIT FOR CALL 1130 causes display screen 950 to display the content shown in FIG. 15.

Figure 15:
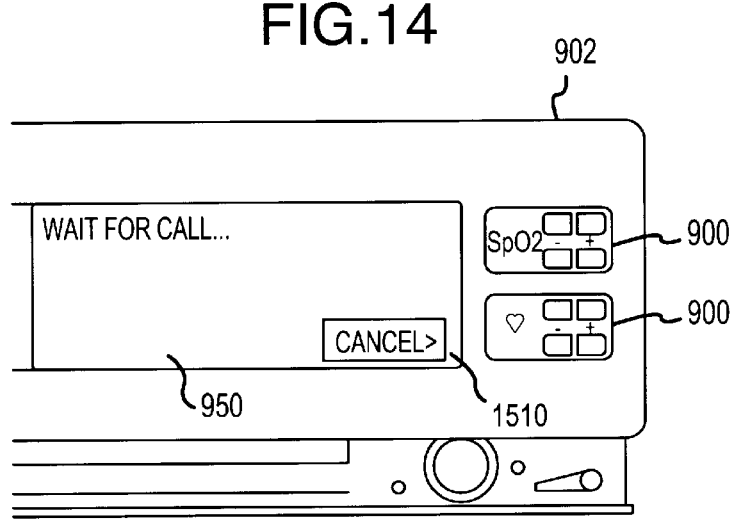

Referring now to FIG. 15, when modem 40 receives a call from remote host system 80, modem 40 arbitrates communication between remote host system 80 and pulse oximeter 30. Pulse oximeter 30 then automatically begins to transmit the selected data to remote host system 80. Screen display 950 will then display the content as shown in FIG. 13. Data is formatted differently when WAIT FOR CALL 1130 is selected as opposed to selecting FAX 1110. Selecting CANCEL 1510 cancels the data sending process and returns the user to the contents of display screen 950 shown in FIG. 9.

Information regarding the patient, doctor, and hospital can be input through user input 15, which in the preferred embodiment uses the same function keys 900 depicted in FIGS. 9 through 15. Function keys 900 are used to select alphanumeric character fields in four lines of data for the inputting of the label information. This function is well-known and has been used on the prior Model 3800 Pulse Oximeter produced by Ohmeda®.

Function keys 900 are also used in conjunction with SETUP MODEM 930 (FIG. 9). In this mode, the user is able to change modem settings. The preferred device is set up to use a predetermined modem, preferably a U.S. Robotics Sportster® modem. Thus, in most cases it is unnecessary for the user to change the modem settings for use of the facsimile function. If SETUP MODEM 930 is selected, the user is able to set the guard tone to either be "none", "550 Hz" of "1800 Hz" using function keys 900. Selection of a "CUSTOM" option (not shown in FIG. 9) under SETUP MODEM enables the user to set the modem initialization string to operate a modem other than the default modem described above.

Figure 16:
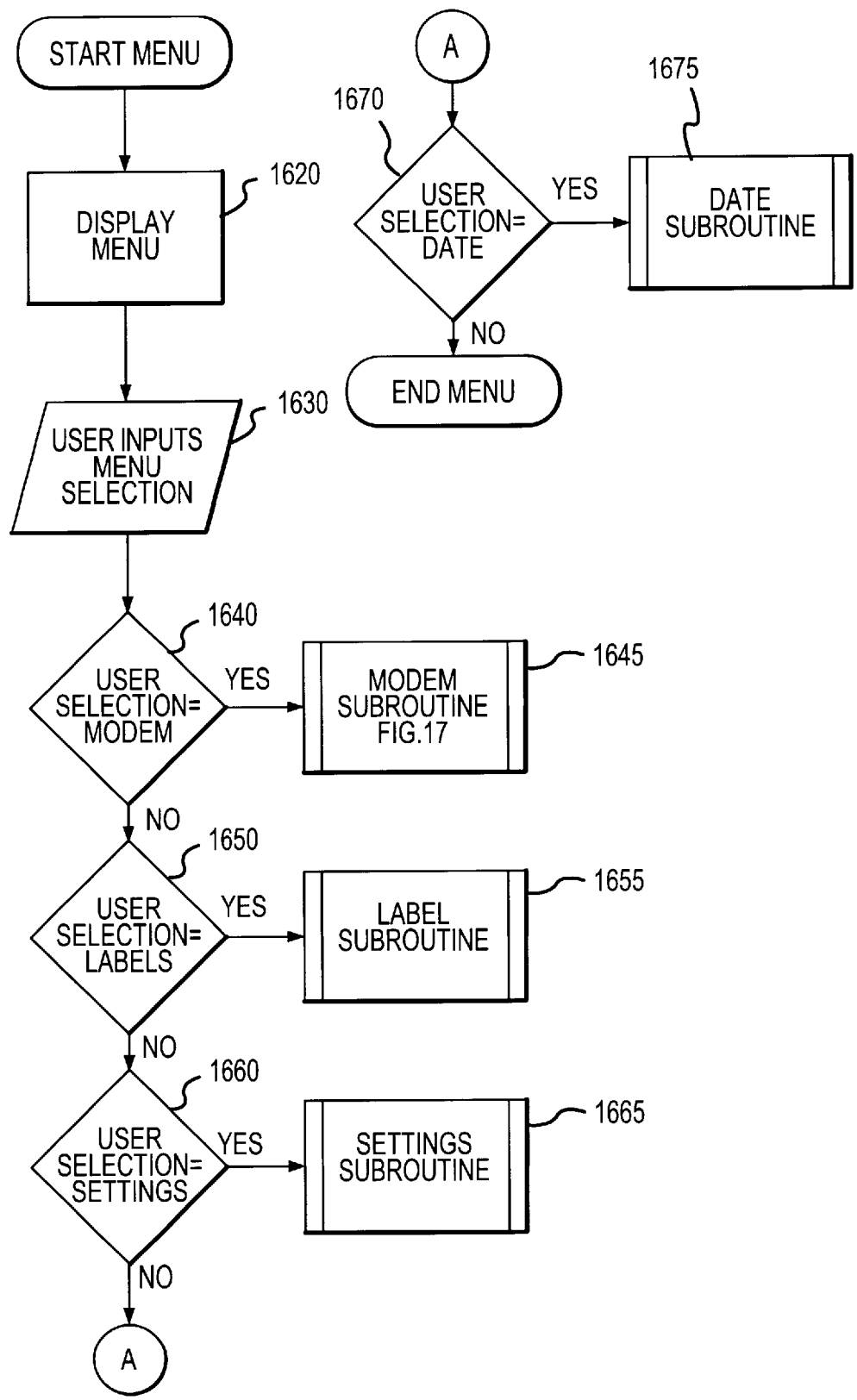
FIGS. 16 through 23 depict a series of software flow diagrams for one embodiment of the present invention.

FIGS. 16 through 23 are flow diagrams which set forth the software control necessary to implement the preferred embodiment of the present invention. Referring now to FIG. 16, the main menu is displayed in step 1620. The user inputs a menu selection in step 1630 which is then polled in steps 1640, 1650, 1660, and 1670. Control is then switched to one of the four subroutines: Modem Subroutine 1645, Label Subroutine 1655, Settings Subroutine 1665, or Date Subroutine 1675. The latter three subroutines are standard subroutines for inputting the patient, doctor, hospital data, changing oximeter settings, and setting the date. Although data stored in main memory 36 from these three subroutines is accessed by the modem analog/serial interface 25 or printer parallel interface 22, they are well-known routines and are not described in detail here.

Figure 17:
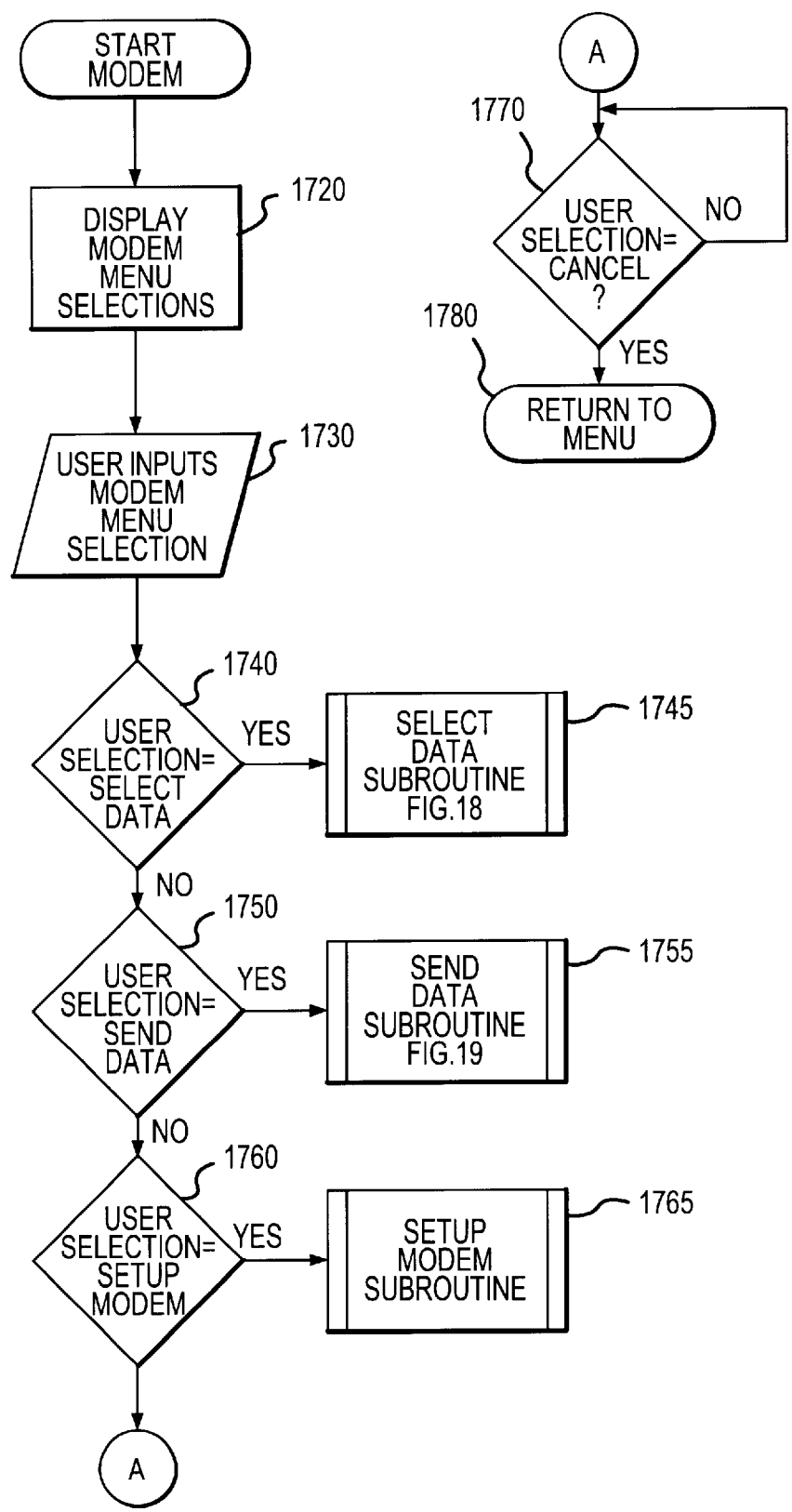

Modem Subroutine 1645 provides access to the modem analog/serial interface 25 and is depicted in greater detail in FIG. 17. Referring now to FIG. 17, upon entering the Modem Subroutine 1645 in FIG. 16, the contents of display screen 950 of FIG. 9 are displayed in step 1720. The user is thereby prompted to enter one of four menu selections in step 1730: SELECT DATA 910, SEND DATA 920, SETUP MODEM 930, OR CANCEL 940 (FIG. 9). The user input is polled in steps 1740, 1750, 1760, and 1770, and control is either switched to the appropriate subroutine or returned to the Main Menu of FIG. 16 at step 1780.

Figure 18:
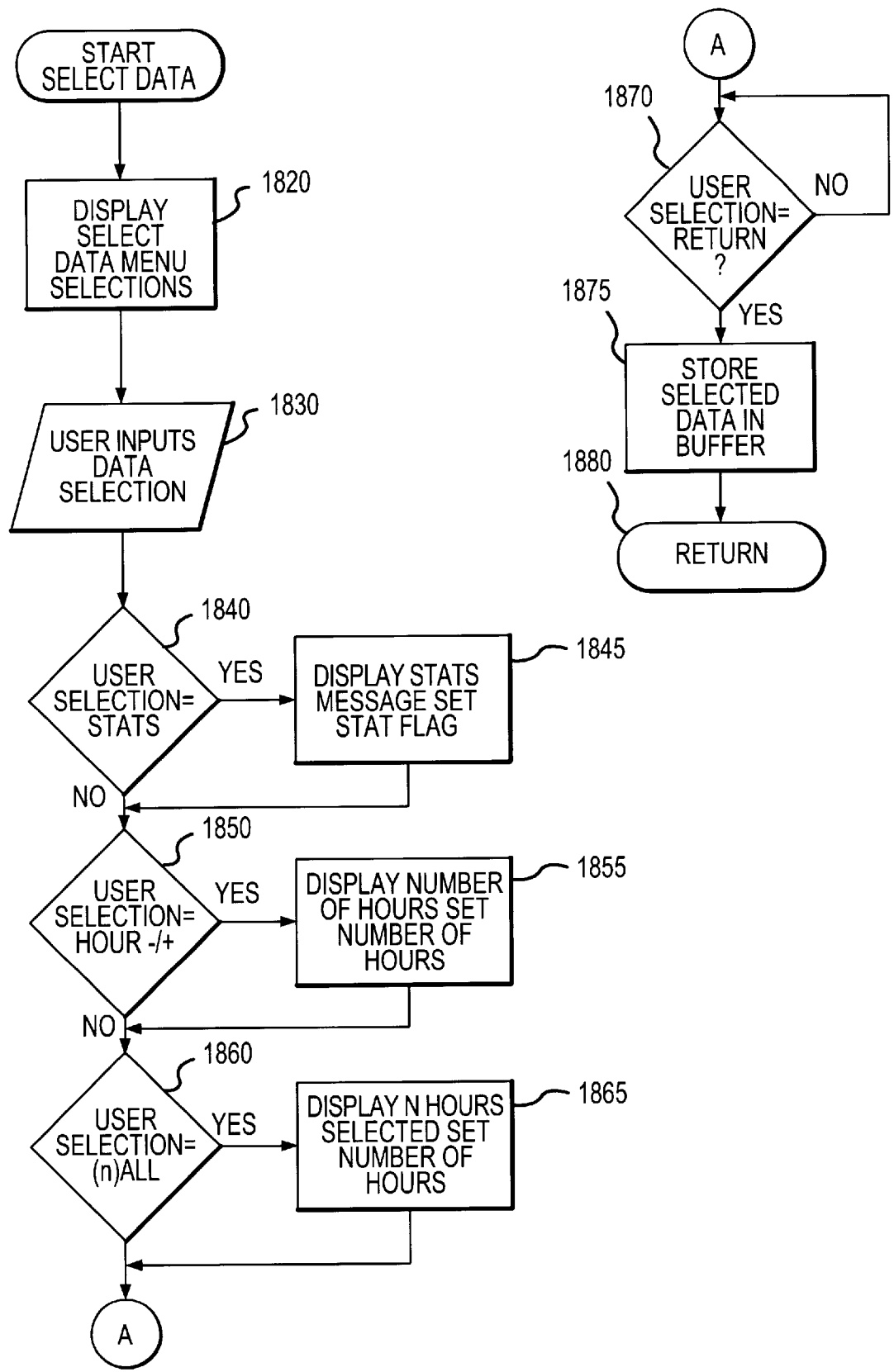

Select Data Subroutine 1745 is depicted in greater detail in FIG. 18. Referring now to FIG. 18, the contents of display screen 950 of FIG. 10 are displayed in step 1820. The user has a choice of four menu selections: HOUR−/+1010, (N)ALL 1020, STATS 1030, or return arrow 1040. The user inputs a selection in step 1830. The user selection is then polled in steps 1840, 1850, 1860, and 1870. Selecting STATS 1030 results in a "STATS" message being displayed to the user and a "STAT FLAG" being set at step 1845. Pulse oximeter 30 will check this flag to determine which data to select for formatting. Selecting STATS 1030 means that only a summary of the data set is provided to the user in the final output rather than all selected data.

If the user selects HOUR−/+1010, the number of hours displayed in display screen 950 can be incremented or decremented in one hour increments in a range from a minimum of one hour to a maximum of twenty-four hours at step 1855. If the user selects (n)ALL 1020 then all of the data available in main memory 36 is indicated for selection in step 1865. Selecting return arrow 1040 results in the selected data being stored in memory buffer 32 (FIG. 1) in step 1875, and control is returned to its calling function at step 1880.

Figure 19:
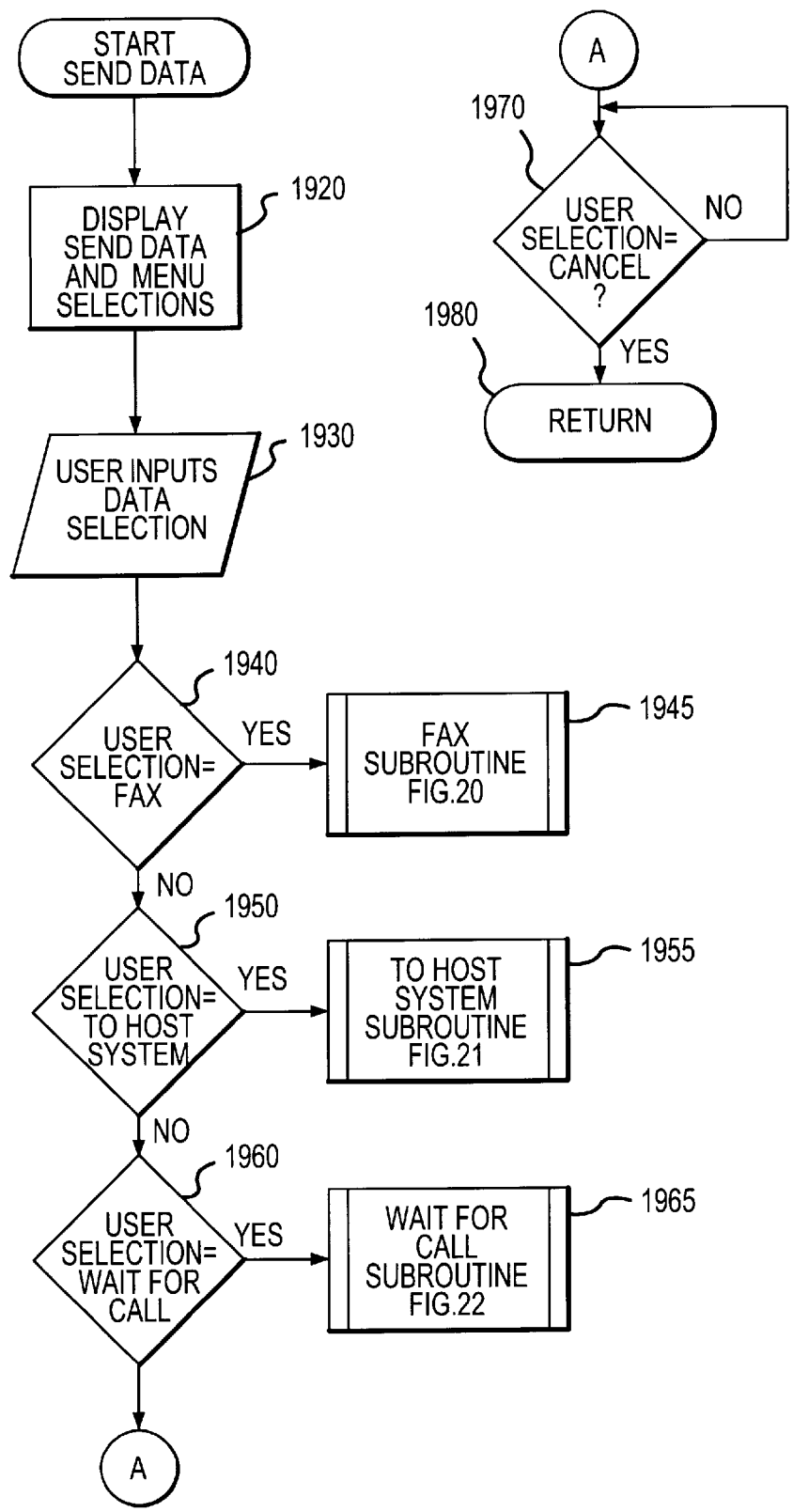

FIG. 19 depicts the flow of software control if the user selects SEND DATA 920 (FIG. 9) in step 1755 of Modem Subroutine of FIG. 17, thereby entering the Send Data Subroutine of FIG. 19. Referring now to FIG. 19, the contents of display screen 950 of FIG. 11 is displayed in step 1920. The user inputs a selection in step 1930 which is then polled in steps 1940, 1950, 1960, and 1970. Control is then switched to one of the three subroutines, or at step 1980 control returns to step 1720 of the Modem Subroutine in FIG. 17.

Figure 20:
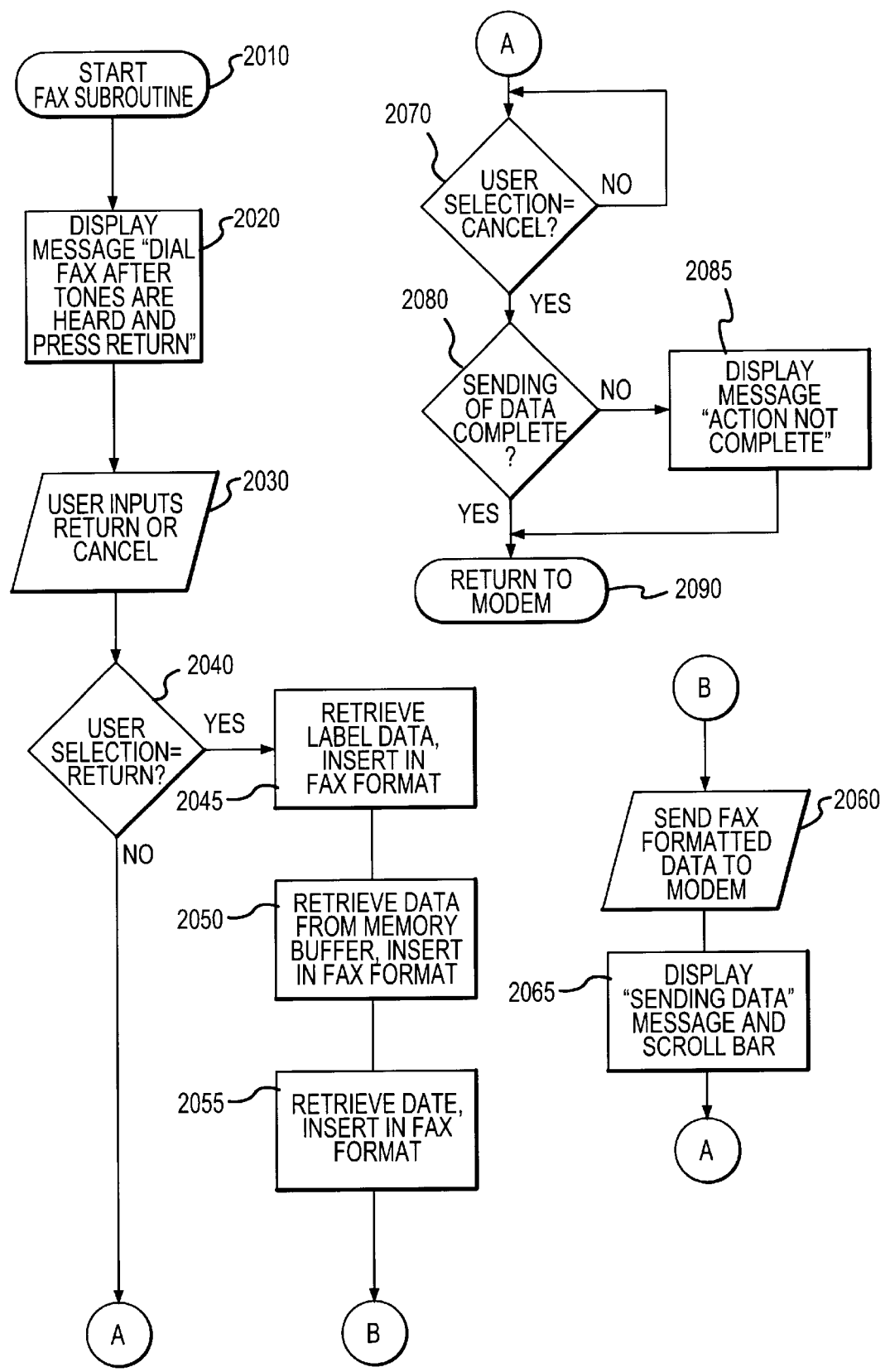

If the check in step 1940 shows that the user has selected Fax 1110 (FIG. 11) in step 1930, then control branches to Fax Subroutine 1945 and is described more fully in FIG. 20. The other two subroutines, To Host System Subroutine 1955 and wait for Call Subroutine 1965, are not part of the facsimile function, rather they are related to standard oximeter to host system connection and host initiated transfer of data. The user returns to step 1720 of the Modem Subroutine in FIG. 17 at step 1980 by selecting CANCEL 1150 (FIG. 11), which is identified in step 1970.

Referring now to FIG. 20, the contents of display screen 950 of FIG. 12 are displayed in step 1920. The message displayed prompts the user to dial the fax telephone number using telephone 50, or in another embodiment, display screen 950 displays blanks for the user to enter the phone number for the remote facsimile 70 using user input 15 internal to pulse oximeter 30. Afterwards, the user is prompted to select return arrow 1210 (FIG. 12) causing the number entered from either method to be dialed. Or, the user may choose CANCEL 1220. Thus, in step 2040 and 2070 the user input from step 2030 is polled awaiting either return arrow 1210 or CANCEL 1220. If return arrow 1210 is selected, then modem analog/serial interface 25 retrieves the information it needs from main memory 36 in order to send data in facsimile data format line by line as described above in the description of FIGS. 6A and 6B. The data is output according to the facsimile report format shown in FIGS. 6A and 6B.

In step 2045 modem analog/serial interface 25 retrieves the label data and inserts it into the facsimile data format line by line. In step 2050, modem analog/serial interface 25 retrieves the data which was previously selected by the user through the Data Selection Subroutine of FIG. 18. This data is then inserted into the facsimile data format line by line. The study date is then retrieved and inserted in the facsimile data format in step 2055. The data in facsimile data format is then sent line by line to the modem 40 and on to the remote facsimile 70 in Step 2060. The contents of display screen 950 of FIG. 13 are displayed in step 2065, which includes a "SENDING DATA" message along with a scroll bar showing the relative amount of time to completion of the transmission. If CANCEL 1310 was selected in step 2070, then in step 2080 a second query determines if the sending of data was completed. If transmission was not complete, then an "ACTION NOT COMPLETE" message is displayed in display screen 950 at step 2085. In step 2090 control is returned to step 1720 of the Modem Subroutine of FIG. 17.

Figure 21:
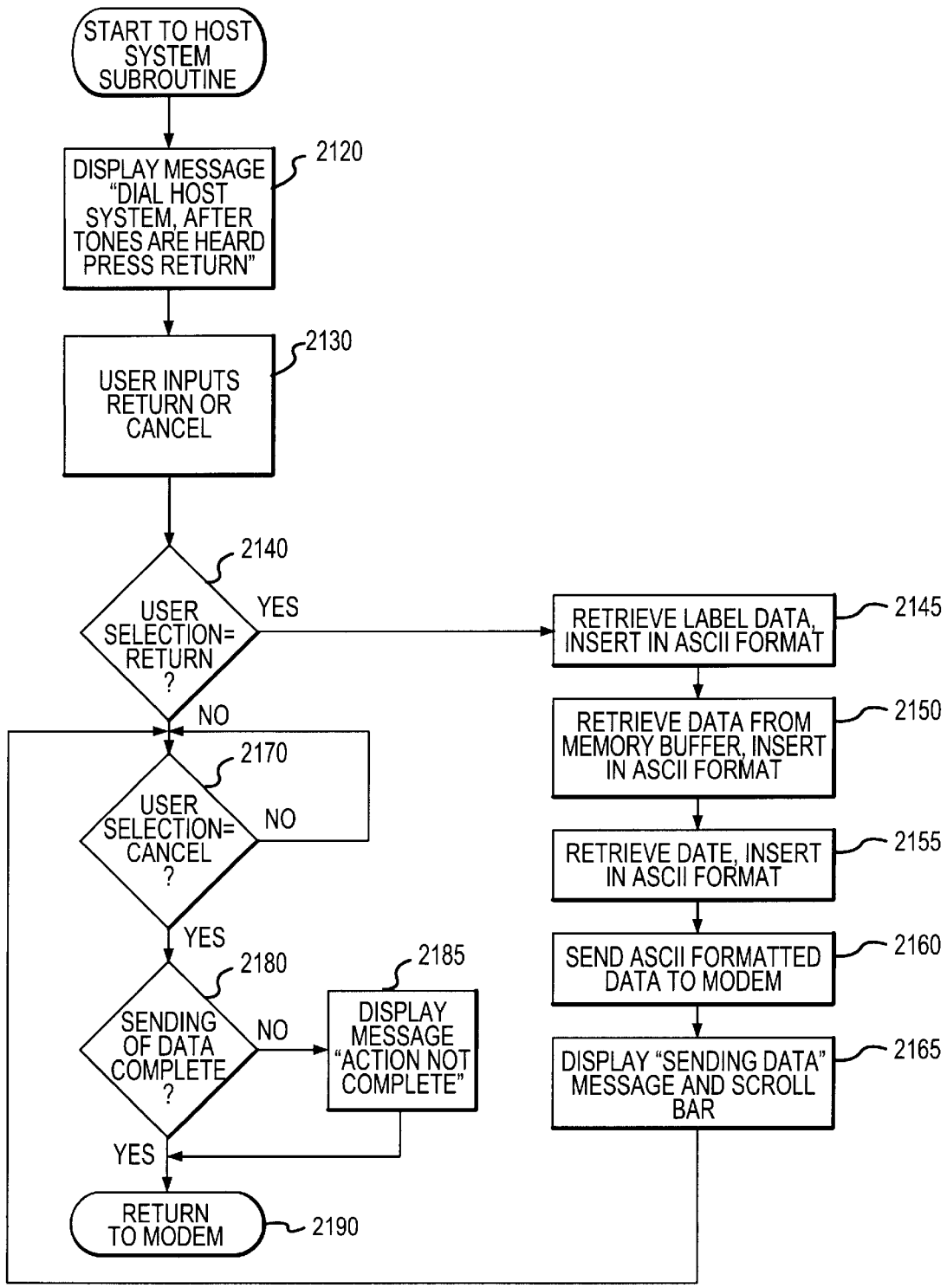

If the user has selected TO HOST SYSTEM 1120 (FIG. 11) in step 1950, then control branches to To Host System Subroutine 1955 and is described more fully in FIG. 21. Referring now to FIG. 21, the contents of display screen 950 of FIG. 14 are displayed in step 2120. The message displayed prompts the user to dial the telephone number of remote host system 80 using telephone 50. The user is also prompted to select return arrow 1410 (FIG. 14) after doing so. Or, the user may choose CANCEL 1420. Thus, in step 2140 and 2170 the user input from step 2130 is polled awaiting either return arrow 1410 or CANCEL 1420. If return arrow 1410 is selected, then modem analog/serial interface 25 retrieves the information it needs from main memory 36 in order to send data in ASCII data format. The data is output according to the remote computer report format shown in FIG. 8.

In step 2145 modem analog/serial interface 25 retrieves the label data and inserts it into the ASCII data format. In step 2150, modem analog/serial interface 25 retrieves the data which was previously selected by the user through the Data Selection Subroutine of FIG. 18. This data is then inserted into the ASCII data format. The study date is then retrieved and inserted in the ASCII data format in step 2155. The data in ASCII data format is then sent to the modem 40 and on to the remote facsimile 70 in Step 2160. The contents of display screen 950 of FIG. 13 are displayed in step 2165, which includes a "SENDING DATA" message along with a scroll bar showing the relative amount of time to completion of the transmission. If CANCEL 1420 was selected in step 2170, then in step 2180 a second query determines if the sending of data was completed. If transmission was not complete, then an "ACTION NOT COMPLETE" message is displayed in display screen 950 at step 2185. In step 2190 control is returned to step 1720 of the Modem Subroutine of FIG. 17.

Figure 22:
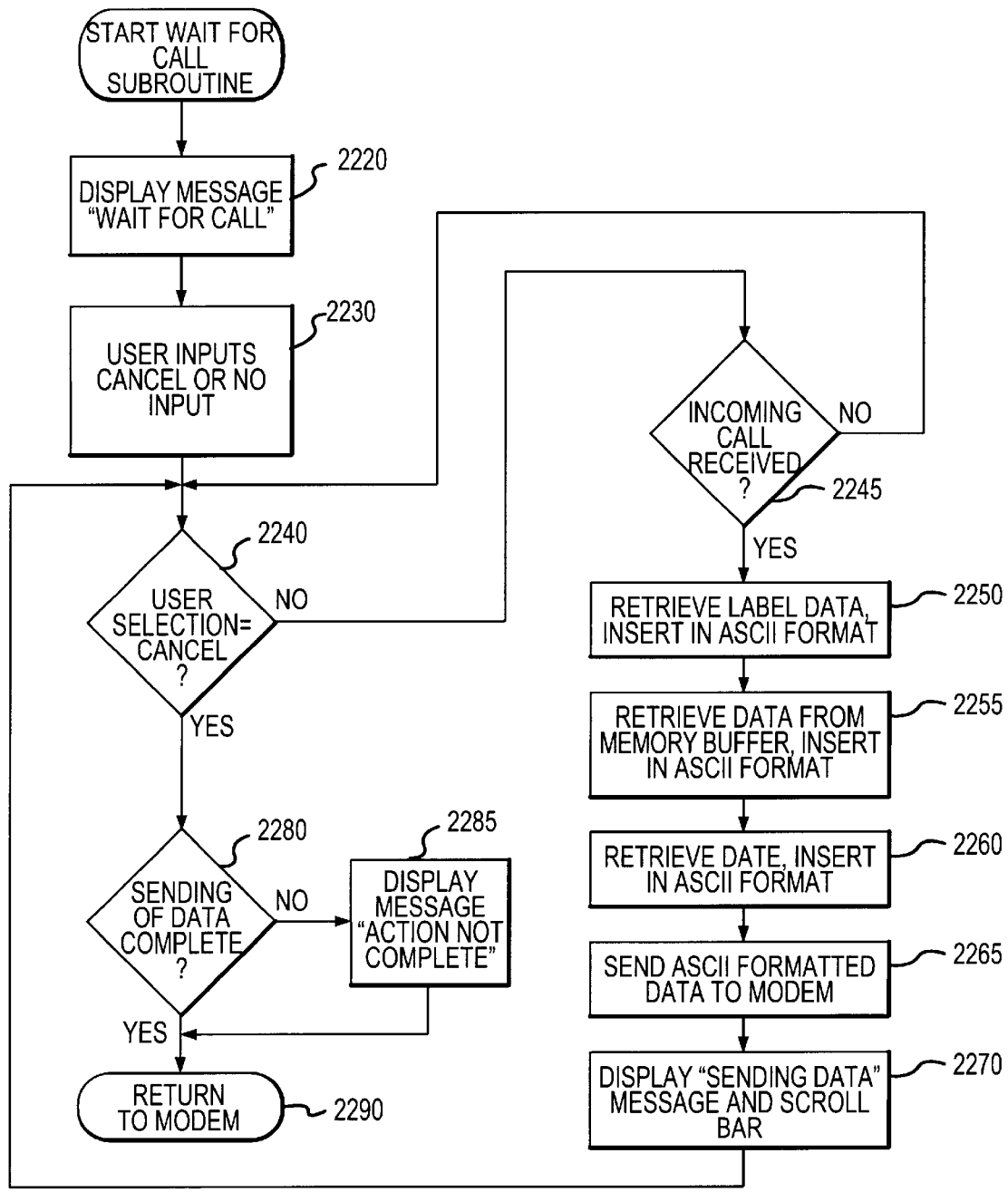

If the user has selected WAIT FOR CALL 1130 (FIG. 11) in step 1960, then control branches to Wait For Call Subroutine 1965 and is described more fully in FIG. 22. Referring now to FIG. 22, the contents of display screen 950 of FIG. 15 are displayed in step 2220. The message displayed indicates that pulse oximeter 30 is in the auto-answer mode and will send the selected data when called by remote host system 80. The user is also prompted to choose CANCEL 1510 at any time in step 2230. Thus, in step 2240 the user input, if any, from step 2230 is polled awaiting CANCEL 1510. If no user input is received, then step 2245 determines if an incoming call from remote host system 80 is received. If no call has been received, control returns to step 2240. If step 2245 determines that remote host system 80 has called, then modem analog/serial interface 25 retrieves the information it needs from main memory 36 in order to send data in ASCII data format as described above in the discussion of FIG. 8. The data is output according to the remote computer report format shown in FIG. 8.

In step 2250 modem analog/serial interface 25 retrieves the label data and inserts it into the ASCII data format. In step 2255, modem analog/serial interface 25 retrieves the data which was previously selected by the user through the Data Selection Subroutine of FIG. 18. This data is then inserted into the ASCII data format. The date is then retrieved and inserted in the ASCII data format in step 2260. The data in ASCII data format is then sent to the modem 40 and on to remote host system 80 in Step 2265. The contents of display screen 950 of FIG. 13 are displayed in step 2270, which includes a "SENDING DATA" message along with a scroll bar showing the relative amount of time to completion of the transmission. If CANCEL 1510 was selected in step 2240, then in step 2280 a second query determines if the sending of data was completed. If transmission was not complete, then an "ACTION NOT COMPLETE" message is displayed in display screen 950 at step 2285. In step 2290 control is returned to step 1720 of the Modem Subroutine of FIG. 17.

Figure 23:
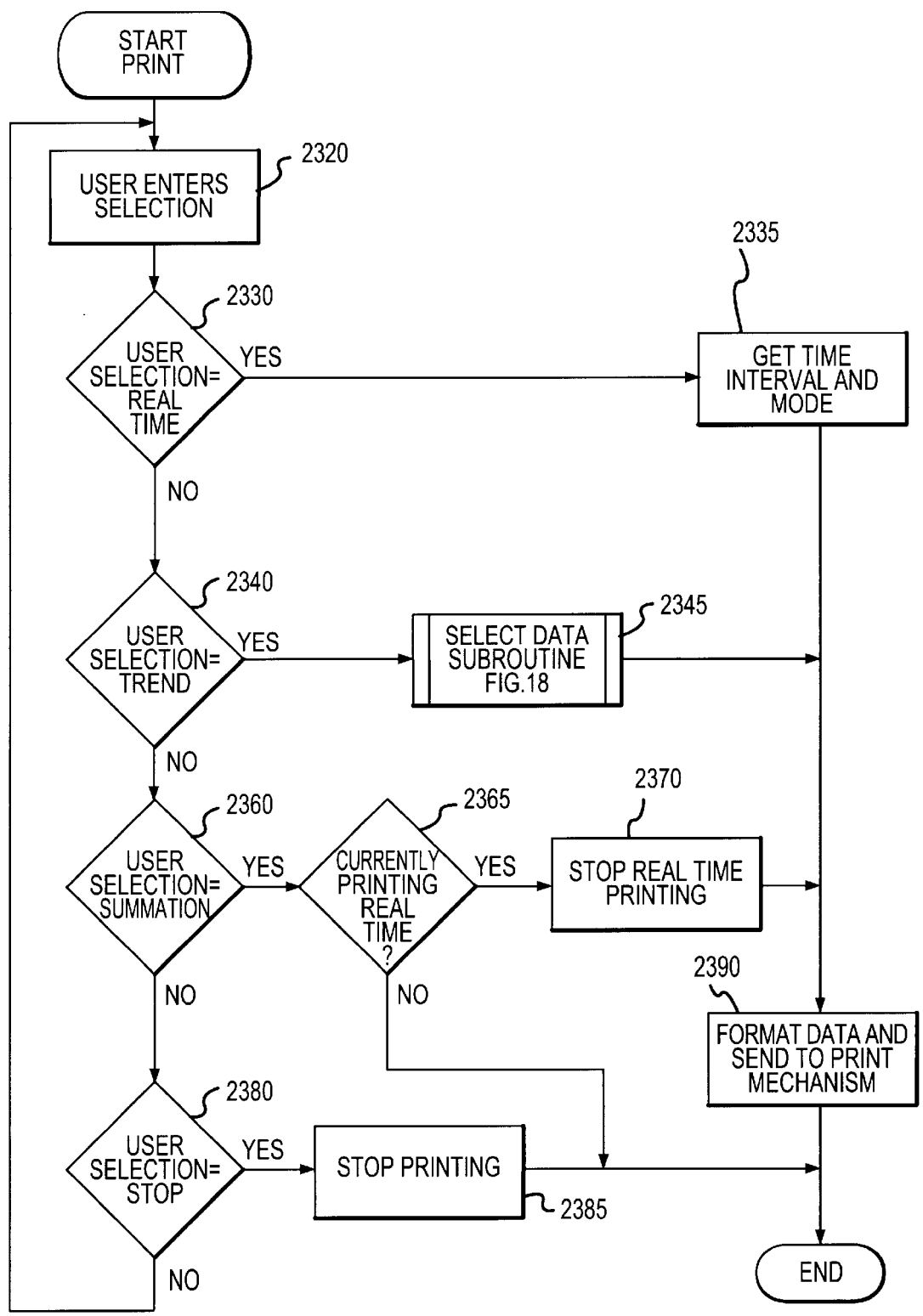

Referring now to FIG. 23, in step 2320 the user may select one of several options using printer user input 24. Thus, in steps 2330, 2340, 2360, and 2280 the user input, if any, from step 2320 is polled. If the check in step 2330 shows that the user has selected real time printing in step 2320, then step 2335 determines the current resolution selection (six second or thirty second) and the current mode setting (SpO$_2$ or PI™). Step 2390 formats the data in ASCII data format according to the determinations in step 2335, and the data in ASCII data format is sent on to print mechanism 23.

If the check in step 2340 shows that the user has selected trend printing in step 2320, then in step 2345 control is switched to the Select Data Subroutine of FIG. 18. After returning from FIG. 18, step 2390 formats in ASCII data format the trend data for the time period established by the Select Data Subroutine, and the data in ASCII data format is sent on to print mechanism 23.

If the check in step 2360 shows that the user has selected summation printing in step 2320, then step 2365 determines if print mechanism 23 is currently printing real time data. If yes, then step 2370 stops the real time printing. Step 2390 then formats in ASCII data format summary statistics for the data that was printed up to the time when the user selected the summation printing option, and the ASCII data format summary statistical data is sent on to print mechanism 23. If step 2365 determines that print mechanism is not currently printing real time data, then the user input in step 2320 is ignored and the print routine ends.

If the check in step 2380 shows that the user has selected stop printing in step 2320, then step 2385 stops any current real time printing or trend printing, and the print routine ends. If the check in step 2380 determines that the user has not selected stop printing, then no user input was entered in step 2320, and control returns step 2320 to await user input.

Thus the apparatus of the present systems enables a user to select a set of photoplethysmographic data for formatting in facsimile data format and transmitting to a remote facsimile machine, formatting in ASCII data format and transmitting to a remote host system, formatting in ASCII data format and transmitting when called by a remote host system, and also formatting in ASCII data format and printing to an internal printer.

While the apparatus disclosed herein illustrates the concepts of the invention, there is no intention to limit the scope of the invention to this specific apparatus. It is expected that those skilled in the art can devise alternate implementations of the display system, which alternate implementations are intended to fall within the scope of the appended claims.

What is claimed is:

1. An apparatus for outputting monitored medical parameters in any of multiple formats comprising:

a photoplethysmographic sensor which monitors a patient and generates analog data corresponding to a plurality of illumination signals detected by said photoplethysmographic sensor;

an analog-to-digital converter which converts at least a portion of said analog data received from said photoplethysmographic sensor into digital data;

a memory for storing said digital data received from said analog-to-digital converter;

a blood oxygen saturation generator for generating a blood oxygen saturation value for said patient derived from said digital data received from said analog-to-digital converter;

a processor in communication with said memory for receiving at least one input instruction requesting a hard copy output regarding said blood oxygen saturation value, to an output device of a specified type, said processor being operative for formatting said output based upon said specified type of said output device in one of a plurality of predefined format types corresponding to said specified type of said output device, each of said format types defining a print layout for said hard copy output on a device-dependent basis; and a network interface for transmission of information regarding said hard copy output across a communication network to said output device.

2. The apparatus of claim 1 further comprising:

a user input for sending said at least one input instruction to said processor, wherein said at least one input instruction causes said processor to format said blood oxygen saturation value in a facsimile data format type.

3. The apparatus of claim 2 further comprising:

a modem analog/serial interface for converting said blood oxygen saturation value in said facsimile data format type received from said processor to an analog signal;

a modem for transmitting said analog signal received from said modem analog/serial interface;

a telephone for transmitting said analog signal received from said modem; and a remote facsimile machine for processing said analog signal from said telephone, wherein said blood oxygen saturation value in said facsimile data format type is printed out on a paper in a facsimile report format, wherein a care giver can use said blood oxygen saturation value of said patient as shown on said paper in said facsimile report format to make medical decisions regarding said patient.

4. The apparatus of claim 1 further comprising: a user input for sending said at least one input instruction to said processor, wherein said at least one input instruction causes said processor to format said blood oxygen saturation value in an ASCII data format type.

5. The apparatus of claim 4 further comprising: a modem analog/serial interface for converting said blood oxygen saturation value in said ASCII data format type received from said processor to an analog signal;
a modem for transmitting said analog signal received from said modem analog/serial interface;
a telephone for transmitting said analog signal received from said modem; and
a remote host system for receiving said analog signal from said telephone, wherein said blood oxygen saturation value in said ASCII data format type is outputted from said remote host system in a remote host system report format, wherein a care giver can use said blood oxygen saturation value of said patient as shown in said remote host system report format to make medical decisions regarding said patient.

6. The apparatus of claim 1 further comprising:
a remote host system for sending said at least one input instruction to said processor, wherein said at least one input instruction causes said processor to format said blood oxygen saturation value in an ASCII data format type.

7. The apparatus of claim 6 further comprising:
a telephone for transmitting said at least one input instruction received from said remote host system;
a modem for transmitting said at least one input instruction received from said telephone; and
a modem analog/serial interface for transmitting said at least one input instruction received from said modem to said processor, wherein said processor converts said blood oxygen saturation value in said ASCII data format type to an analog signal and transmits said analog signal through said modem analog/serial interface through said modem through said telephone and to said remote host system, wherein said blood oxygen saturation value in said ASCII data format type is outputted from said remote host system in a remote host system report format, wherein a care giver can use said blood oxygen saturation value of said patient as shown in said remote host system report format to make medical decisions regarding said patient.

8. The apparatus of claim 1 further comprising:
a printer user input for sending said at least one input instruction to said processor, wherein said at least one input instruction causes said processor to format said blood oxygen saturation value in an ASCII data format type.

9. The apparatus of claim 8 further comprising:
a printer parallel interface for converting said blood oxygen saturation value in said ASCII data format type to a digital parallel signal; and
a printer mechanism for processing said digital parallel signal, wherein said blood oxygen saturation value in said ASCII data format type is printed out on a paper in an internal printer report format, wherein a care giver can use said blood oxygen saturation value of said patient as shown in said internal printer report format to make medical decisions regarding said patient.

10. An apparatus for the transmittal of monitored photoplethysmographic data to a remote facsimile machine at a medical facility of a monitoring physician such that a patient requiring photoplethysmographic monitoring but not otherwise requiring continuous care at the medical facility of the monitoring physician can be discharged from or otherwise reside separate from the medical facility at a patient location, said apparatus comprising:

(a) a photoplethysmographic unit, disposed at the patient location separate from the medical facility, including
(1) a photoplethysmographic sensor which monitors the patient by detecting illumination signals from a tissue of the patient and generates analog data from said illumination signals;
(2) an analog-to-digital converter which coverts at least a portion of said analog data received from said photoplethysmographic sensor into digital data sets based on said illumination signals;
(3) a memory wherein a plurality of digital data sets are stored; and
(4) a blood oxygen content generator which generates a set of one or more medical parameters regarding a blood oxygen content of the patient from said plurality of digital data sets; and (b) a facsimile transmission unit, disposed at the patient location separate from the medical facility, including
(1) a photoplethysmographic formatting module for generating an output report for conveying information regarding said set of one or more medical parameters in a form suitable for review by the monitoring physician and formatting said output in a facsimile format with formatting elements for defining hard copy lines and at least one page wherein said report includes multiple sections and each section includes one line and a first section of said hard copy report is formatted and transmitted prior to formatting of a second section of said report; and
(2) a facsimile destination logic for programming into said facsimile transmission unit information regarding a destination mode of a telecommunications network for transmission of a hard copy image of said output, said facsimile destination logic being operative for selecting a destination mode of the medical facility of the monitoring physician for direct transmission of said output to the monitoring physician;

wherein, said set of one or more medical parameters may be received by the remote facsimile machine at the medical facility for printing said hard copy image of said output presenting said set of one or more medical parameters, whereby the monitoring physician can use said hard copy image of said set of one or more medical parameters to make medical decisions regarding the patient based on said blood oxygen content of the patient as reflected in said set of one or more medical parameters presented in said hard copy image.

11. The apparatus of claim 10 further comprising a modem for transmitting said set of one or more medical parameters in said facsimile format over a standard telephone line to the remote facsimile machine.

12. The apparatus of claim 10 further comprising a means for wireless communication for transmitting said set of one or more medical parameters in said facsimile format to the remote facsimile machine.

13. The apparatus of claim 12 wherein said means for wireless communication is a cellular telephone for transmitting said set of one or more medical parameters in said facsimile format to the remote facsimile machine via a standard cellular telephone connection.

14. The apparatus of claim 12 wherein said means for wireless communication is a digital PCS telephone for transmitting said set of one or more medical parameters in said facsimile format to the remote facsimile machine via a standard digital PCS telephone connection.

15. The apparatus of claims 12 wherein said means for wireless communication is a satellite link for transmitting said set of one or more medical parameters in said facsimile format to the remote facsimile machine.

16. The apparatus of claim 10 wherein said set of one or more medical parameters is selected from the set consisting of: blood oxygen concentration, pulsatility value, and pulse rate.

17. The apparatus of claim 10 wherein said set of one or more medical parameters is selected from the set consisting of: blood oxygen concentration, blood carbon dioxide concentration, methemoglobin concentration, pulsatility value, and pulse rate.

18. The apparatus of claim 10 wherein said set of one or more medical parameters is selected from the set consisting of: patient's name, hospital name, doctor's name, date, time of test, lowest blood analyte level, highest blood analyte level, lowest pulse rate, highest pulse rate, high pulse rate duration, low pulse rate duration, recording duration, low blood analyte level duration, sensor off alarm, no sensor alarm, pulsatility value, blood analyte concentration value, blood analyte concentration by range, blood analyte concentration histogram, blood analyte concentration event chart, and average blood analyte concentration.

19. The apparatus of claim 10 further comprising a user input consisting of a plurality of function keys for inputting selections regarding said set of one or more medical parameters to be formatted in said facsimile format.

\* \* \* \* \*